(12) United States Patent
Burnett et al.

(10) Patent No.: US 7,531,521 B2
(45) Date of Patent: *May 12, 2009

(54) FORMULATION FOR USE IN THE PREVENTION AND TREATMENT OF CARBOHYDRATE INDUCED DISEASES AND CONDITIONS

(75) Inventors: Bruce P. Burnett, Centennial, CO (US); Qi Jia, Superior, CO (US)

(73) Assignee: Unigen Pharmaceuticals, Inc., Lacey, WA (US)

( * ) Notice: Subject to any disclaimer, the term of this patent is extended or adjusted under 35 U.S.C. 154(b) by 207 days.

This patent is subject to a terminal disclaimer.

(21) Appl. No.: 10/785,704

(22) Filed: Feb. 24, 2004

(65) Prior Publication Data

US 2004/0186062 A1 Sep. 23, 2004

Related U.S. Application Data

(63) Continuation-in-part of application No. 10/462,030, filed on Jun. 13, 2003, which is a continuation-in-part of application No. 10/427,746, filed on Apr. 30, 2003.

(60) Provisional application No. 60/450,922, filed on Feb. 26, 2003.

(51) Int. Cl.
*A61K 31/70* (2006.01)
(52) U.S. Cl. ............................ 514/33; 514/35; 514/451
(58) Field of Classification Search .................. 514/33, 514/35, 451
See application file for complete search history.

(56) References Cited

U.S. PATENT DOCUMENTS

| 5,650,432 | A | 7/1997 | Walker |
| 5,886,029 | A | 3/1999 | Dhaliwal |
| 6,080,401 | A | 6/2000 | Reddy et al. |
| 6,083,921 | A | 7/2000 | Xu |
| 6,093,403 | A | 7/2000 | Huo et al. |
| 6,475,530 | B1 * | 11/2002 | Kuhrts ......................... 424/725 |
| 6,576,660 | B1 * | 6/2003 | Liao et al. .................... 514/456 |
| 2003/0105030 | A1 | 6/2003 | Liao et al. |

FOREIGN PATENT DOCUMENTS

| CN | 1043406 C | 5/1999 |
| EP | 0742012 A2 | 11/1996 |
| EP | 09568674 A1 | 11/1999 |
| FR | 2651132 | 3/1991 |
| JP | 403240725 | 10/1991 |
| JP | 2002053484 | 2/2002 |
| WO | WO 00/59523 | 10/2000 |

OTHER PUBLICATIONS

Boozer et al. (2001) International Journal of Obesity, 25:316-324.
Kuppusamy and Das (1992) Biochem. Pharmacol. 44:1307-1315.
Kuppusamy and Das (1994) Biochem. Pharmacol. 47:521-529.
Morimoto et al. (2001) Nippon Yakurigaku Zasshi 117:77-86 (*English Abstract*).
Murase et al. (2002) International Journal of Obesity, 26:1459-1464.
Yoshida et al. (1995) International Journal of Obesity 19:717-722.
Hong et al. (2001) Biochemical Pharmacology 62:1175-1183.
Kim et al. (1990) Yakhak Hoeji 34(5):348-364.
Chou et al. (2003) Anesth. Analg 97:1724-1729, The Antiinflammatory and Analgesic Effects of Baicalin in Carrageenan-Evoked Thermal Hyperalgesia.
Krakauer et al. (2001) FEBS Letters 500 52-55, The flavonoid baicalin inhibits superantigen-induced inflammatory cytokines and chemokines.
Nakamura (Aug. 2003) Exp Eye Res 77(2):195-202, Effects of baicalin, baicalein, and wogonin on interleukin-6 and interleukin-8 expression, and nuclear factor-kappab binding activities induced by interleukin-1beta in human retinal pigment epithelial cell line (abstract only).
Nakagami (Aug. 22, 1995) abstract Database WPI Week 199519 Aug. 22, 1995, Derwent Publications Ltd., London, GB; Class 954,p. 2, AN 1995-325471 XP002418722 Nakagami T; Nakamura T; Tamura N: "Anti-complementary substance used as therapeutic agent—comprises gallic acid, methyl gallate, acetyl-salicylic acid, caffeic acid, catechin, epi-gallo-catechin gallate, myricetin, quercitrin and/or baicalein, or their salts" & JP 07 223941 A ((NIHA-N) Nippon Ham KK).
Hase et al. (Mar. 19, 2002) abstract, Database WPI Week 200242, Derwent Publications Ltd., London, GB: AN 2002-388616 XP002422560 & JP 2002 080362 A (Kao Corp) "Natural products derived PPAR dependent gene activators".

* cited by examiner

*Primary Examiner*—Elli Peselev
(74) *Attorney, Agent, or Firm*—Swanson & Bratschun, L.L.C.

(57) ABSTRACT

The present invention provides a novel method for inhibiting sugar-induced weight gain resulting from fructose and glucose driven lipogenesis. The method for inhibiting sugar-induced weight gain is comprised of administering a composition comprising a mixture of Free-B-Ring flavonoids and flavans synthesized and/or isolated from a single plant or multiple plants, preferably in the *Scutellaria* and *Acacia* genus of plants to a host in need thereof. The present also includes novel methods for the prevention and treatment of diseases and conditions resulting from high carbohydrate ingestion. The method for preventing and treating these sugar-induced diseases and conditions is comprised of administering to a host in need thereof a therapeutically effective amount of a composition comprising a mixture of Free-B-Ring flavonoids and flavans synthesized and/or isolated from a single plant or multiple plants, preferably in the *Scutellaria* and *Acacia* genus of plants and a pharmaceutically acceptable carrier.

10 Claims, 15 Drawing Sheets

FORMULATION FOR USE IN THE PREVENTION AND TREATMENT OF CARBOHYDRATE INDUCED DISEASES AND CONDITIONS

FIELD OF THE INVENTION

This invention relates generally to the use of a composition of matter formulated for use in preventing and treating diseases and conditions resulting from high carbohydrate ingestion. Specifically, the present invention relates to a novel composition of matter comprised of a mixture of a blend of two specific classes of compounds—Free-B-Ring flavonoids and flavans—for use in the prevention and treatment of weight gain and obesity, as well as, other diseases and conditions resulting from high carbohydrate ingestion. The diseases and conditions include, but are not limited to, hyperlipidemia, high cholesterol, arteriosclerosis, atherosclerosis, syndrome X (metabolic syndrome), hypertension and systemic inflammation conditions caused by obesity and diabetes.

BACKGROUND OF THE INVENTION

Energy in the body is generated by the production of ATP from "food stuff." More specifically, when food is consumed it is broken down into its constituent parts consisting primarily of simple and complex carbohydrates, fats, proteins and indigestible fiber such as cellulose. The carbohydrates, fats and proteins are then further broken down into their basic units: carbohydrates into simple sugars, proteins into amino acids and fats into fatty acids and glycerol. The body then uses these basic units to generate substances it needs for growth, maintenance and energy production. Carbohydrates, proteins and fats can all be metabolized to provide energy in the form of ATP, however, carbohydrates are the primary substrates used by the body for the generation of ATP via glycolysis and the Kreb's cycle.

Depending on the size of the molecule carbohydrates are classified as either simple or complex. Simple carbohydrates are small molecules, specifically mono- and disaccharides, such as glucose, fructose, galactose and sucrose. Complex carbohydrates or polysaccharides are comprised of long chains of simple carbohydrates. The most important polysaccharides are starch, glycogen and cellulose, which are all polymers of glucose differing only in the way the glucose molecules are linked. Glycogen is the energy reservoir in animals, starch is the energy reservoir in plants and cellulose is the major structural component of plants. While most forms of starch are digestible, humans lack the enzyme necessary to digest cellulose and therefore it becomes part of our dietary fiber.

Over half of the carbohydrates consumed by humans have traditionally come from starch sources such as breads and grains. Starch is a mixture of amylose and amylopectin. Amylose is a linear polysaccharide consisting of glucose molecules covalently bonded by $\alpha$-1,4 linkages. Amylopectin is a branched polysaccharide consisting of glucose molecules covalently bonded with one $\alpha$-1,6 linkage per approximately thirty $\alpha$-1,4 linkages. Starch is rapidly hydrolyzed by $\alpha$-amylase, which is secreted by the salivary glands and the pancreas. Upon hydrolysis, amylose is broken down into small straight chain oligosaccharides, such as maltose (two glucose molecules in a $\alpha$-1,4 linkage) and maltotriose (three glucose molecules in $\alpha$-1,4 linkages). Amylopectin is broken down into small straight chain oligosaccharides, as well as, into the branched oligosaccharide $\alpha$-dextrin (several glucose molecules linked by both $\alpha$-1,4 linkages and $\alpha$-1,6 linkages). These sugars are further broken down into glucose monomers by the enzymes maltase and $\beta$-amylase.

Other carbohydrates consumed in our diet are simple carbohydrates, such as the monosaccharides glucose and fructose and the disaccharide sucrose. Glucose is present in low levels in most natural foods, whereas fructose is obtained primarily from processed foods, sweeteners and to a minor extent from fruits and certain vegetables. Fructose is produced synthetically via the enzymatic isomerization of dextrose. (Bhosale et al. (1996) Microbiol. Rev. 60:280-300). Sucrose, another well known sweetener, is comprised of a glucose and a fructose in an $\alpha$-1,2 linkage between C1 of glucose and C2 of fructose. Sucrose is hydrolyzed by the enzyme sucrase in the intestinal mucosa to provide glucose and fructose. (Dahlqvist (1972) Acta Med. Scand. Suppl. 542:13-18).

Insulin is a hormone secreted by the $\beta$-cells of the pancreas which enables the body to use glucose for energy. One of the key metabolic actions of the hormone insulin is to control blood sugar levels by promoting glucose uptake into fat and muscle cells. Briefly, when glucose enters cells, stimulated by insulin, there is an up-regulation of GLUT4 glucose transporter protein, which accumulates on the surface of the cells, particularly muscle and fat cells. (Furtado et al. (2002) Biochem. Cell. Biol. 80:569-578). Elevated cell surface levels of GLUT4 then facilitates enhanced glucose uptake from the circulation and storage in fat and muscle tissue. With reference to FIG. 1, upon uptake glucose is immediately converted to glucose 6-phosphate by the enzyme, hexokinase D also known as glucokinase, which adds a phosphoryl group from ATP to C6 of glucose thereby producing ADP and glucose 6-phosphate. Glucose 6-phosphate is then converted to fructose 6-phosphate, which is converted to fructose 1,6-diphosphate by the action of phosphofructokinase, which adds a phosphoryl group to C1 from a second molecule of ATP. The enzyme aldolase B (aldolase) then converts fructose 1,6-diphosphate to dihydroxyacetone phosphate and glyceraldehyde 3-phosphate, a substrate suitable for the final conversion to pyruvate, which is then converted to acetyl CoA upon entry into the Kreb's cycle. Additional glyceraldehyde 3-phosphate is produced from dihydroxyacetone phosphate by the action of the enzyme triose phosphate isomerase. Thus, during the process of glycolysis, two ATP are expended initially, but two ATP are formed later in the process, as well as one molecule of NADH per glucose molecule, which is eventually converted to provide a net production of three ATP molecules.

When the amount of glucose present in the blood exceeds the current energy demand it can be stored in the liver and muscle as glycogen or it can be converted to triglycerides, primarily in the liver and transferred to adipose tissue for storage. Lipogenesis includes processes of fatty acid synthesis and subsequent triglyceride synthesis. Conversely, when glucose levels in the blood become to low, the process is reversed and glucose is generated from acetyl Co-A and pyruvate. Gluconeogenesis refers to the process of generating glucose from acetyl-CoA and pyruvate and is essentially the reverse of glycolysis. Gluconeogenesis, like lipogenesis also occurs primarily in the liver and is the means by which glucose is generated and secreted into the blood stream for use by cells in the body.

Fructose, a constituent of sucrose and the primary sweetener and preservative added to processed foods over the last twenty years (Hanover and White (1993) Am. J. Clin. Nutr. 58(Supp.):724S-732S; Park and Yeltley (1993) Am. J. Clin. Nutr. 58(Supp.):737S-747S), is also used as a major source of energy by the body, but it enters the glycolysis pathway via a different mechanism. Fructose, unlike glucose, bypasses the need for insulin and is shunted directly into the glycolysis pathway. (Elliott et al. (2002) Am. J. Clin. Nutr. 76:911-922). As soon as fructose enters the bloodstream, the vast majority of it (approximately 70%) is absorbed by the liver through the portal vein. (Toppings and Mayes (1971) Nutr. Metab. 13:331-338; Mayes (1993) Am. J. Clin. Nutr. 58(Supp.): 754S-765S). Fructose is processed primarily in the liver, via the fructose 1-phosphate pathway. With reference to FIG. 1, the first step in this pathway is the phosphorylation of fructose to fructose 1-phosphate by the action of fructokinase, which adds a phosphoryl group from ATP to C1 of fructose thereby producing ADP and fructose 1-phosphate. (Hers (1952) Biochim. Biophys. Acta 8:416-423). Fructose-1-phosphate is then converted to glyceraldehyde and dihydroxyacetone phosphate. This aldol cleavage is catalyzed by a specific fructose 1-phosphate aldolase. The glyceraldehyde is then converted to glyceraldehyde 3-phosphate for entry into the glycolysis pathway, requiring the input of second ATP molecule. Additionally, dihydroxyacetone phosphate is converted to glyceraldehyde 3-phosphate by the action of triose phosphate isomerase for entry into the glycolysis pathway. This process requires two ATP molecules. The selective, rapid uptake and utilization of fructose by the liver is due to the presence in liver cells of the enzyme fructokinase, which is lacking in most other tissues (i.e., adipose and muscle). (Van den Berghe (1986) in: *Metabolic Effects of Dietary Carbohydrates. Progress in Biochemical Pharmacology* (Mcdonald & Vrana, eds), 21:1-32, Karger, Basel, Switzerland; Hallfrisch (1987) in: *Metabolic Effects of Dietary Fructose* (Reiser & Hallfrisch, eds), pp. 25-40, CRC Press, Boca Raton, Fla.).

Alternatively, fructose can be phosphorylated to fructose 6-phosphate by the enzyme hexokinase, which occurs primarily in the kidneys, adipose tissue and skeletal muscle. It is estimated that approximately 20% of ingested fructose is immediately processed by the kidneys, while approximately 10% is quickly absorbed by adipose tissue and skeletal muscle. (Froesch and Ginsberg (1962) J. Biol. Chem. 237: 3317-3324; Bergstrom and Hultman (1967) Acta Med. Scand. 182:93-107). Most of the fructose in the kidneys, adipose tissue and skeletal muscle is metabolized via fructose 6-phosphate. Consequently, at any given time, there is a very low concentration of fructose circulating in the bloodstream. (Macdonald and Turner (1968) Lancet 1:841-843; Crossley and Macdonald (1970) Nutr. Metab. 12:171-178). Intestinal uptake of fructose is less than that of glucose or sucrose, however glucose stimulates a strong absorption response of fructose by the intestinal mucosa. (Truswell et al. (1988) Am. J. Clin. Nutr. 48:1424-1430). High fructose levels do not appear to cause any observable increase in circulating glucose levels. (Schwarz et al., 1992; Tounian et al. (1994) Am. J. Physiol. 267:E710).

Calories resulting from fat consumption have decreased steadily over the past thirty years (Kennedy et al. (1999) J. Am. Coll. Nutr. 18:207-212), while dietary starch or complex carbohydrate intake has remained rather constant. Contrary to these trends, however, there has been a tremendous increase the use of added sugar by the food and beverage industries. Coupled with an increased amount of calories from sugar obtained from sources outside the home, the majority of calories in the modern, industrial diet come from sugar and complex carbohydrate sources. (Krebs-Smith (2001) J. Nutr. 131:527S-535S; Nielsen et al. (2002) Prev. Med. 35:107-113).

Over the past thirty years, there has also been approximately a 40% drop in the use of cane and sugar beet sweeteners. (Kanter (1998) "A dietary assessment of the US Food Supply: Comparing per capita food consumption with food guide pyramid serving recommendations," from the Food and Rural Economics Division, Economics Research Service, U.S. Department of Agriculture, Agricultural Economic Report no. 772). Alternatively, there has been about a 300% increase in the use of high fructose corn sweeteners. The principal reason for the shift from sucrose to fructose as the primary sweetener in the western world is likely due to economics. Fructose is sweeter than both sucrose and glucose and is also easier and cheaper to produce. Fructose corn sweeteners have become the primary food additive in the American diet over the past twenty years with soft drinks and fruit drinks accounting for 43-44% of the added fructose. (Kanter (1998) "A dietary assessment of the US Food Supply: Comparing per capita food consumption with food guide pyramid serving recommendations," from the Food and Rural Economics Division, Economics Research Service, U.S. Department of Agriculture, Agricultural Economic Report no. 772). Total sugar consumption is still rising due entirely to the addition of high fructose corn syrup to processed foods. (Krebs-Smith (2001) J. Nutr. 131:527S-535S).

The health effects of added sugar, specifically fructose, were not realized before its use became ubiquitous in processed foods. Fructose usage over the last twenty years has coincided with a dramatic increase in obesity and diabetes. (Flegal et al. (1998) Int. J. Obes. 22:39-47). As discussed in detail below, studies have now revealed that the chronic, long-term effects of increased sugar, particularly fructose, consumption may be extremely harmful with respect to carbohydrate utilization, purine metabolism, premature aging and lipid metabolism. Additionally, the resulting obesity produces a sustained inflammatory effect in the body with the production of pro-inflammatory cytokines such as tumor necrosis factor (TNFα), interleukin-6 (IL-6) and C-reactive protein (CRP).

The production of TNFα and IL-6 are regulated by the transcription factor NFκB. NFκB plays an important role in the regulation of systemic inflammation and its relationship to sugar-induced obesity and the subsequent generation of disease (Lebovitz (2003) Int. J. Clin. Pract. Suppl. 134:18-27). Activation of NFκB is part of a stress response activated by several biological processes including growth factors, lymphokines, cytokines, UV radiation, pharmacological agents and diet. (Spencer et al. (1997) Int. Immunol. 9:1581-1588). In its inactive form, NFκB is largely contained in the cytoplasm, bound by the IκB family of inhibitor proteins. Dietary changes such as increased fructose uptake can activate NFκB and cause phosphorylation of IkB thus releasing NFκB which allows translocation of the molecule to the nucleus. In the nucleus, NFκB binds with a consensus sequence (5' GGGACTTTCC-3') of various genes, activating their transcription. In systemic inflammation caused by sugar-induced obesity, this leads to increased expression of TNFα and IL-6. This increase in these pro-inflammatory proteins then induces an increase in CRP.

It has been reported that continuous high use of fructose as an energy source disrupts carbohydrate metabolism leading to a decrease in the use of starch and glucose by many tissues. (Bender and Thadini (1970) Nutr. Metab. 12:22-39; Tuovinen and Bender (1975) Nutr. Metab. 19:161-172). Specifically, the continuous consumption of fructose results in the down-regulation of hexokinase and the up-regulation of glucose-6-phosphatase in the liver (see FIG. 1; Freedland and Harper (1957) J. Biol. Chem. 228:743-751). This adaptive response leads to a decrease in the conversion of glucose to liver glycogen. (Vrana et al. (1978) Nutr. Metab. 22:262-268;

Vrana et al. (1978) Nutr. Metab. 22:313-320). In the pancreas, fructose does not up-regulate insulin production due to low concentrations of fructose transporter GLUT5 protein in β cells (Grant et al. (1980) Diabetologia 19:114-117; Curry (1989) Pancreas 4:2-9; Sato et al. (1996) Tissue Cell 28:637-643). This leads to elevated blood glucose over time and insulin insensitivity, the principal cause of Type II diabetes. The liver can use fructose to generate glycogen via an adaptive enzyme response, but at a much lower level than glucose can be converted to glycogen. (Freedland and Harper (1957) J. Biol. Chem. 228:743-751). Additionally, increased and chronic consumption of sucrose or fructose leads to an increased ability of the liver to synthesize fatty acids, thereby decreasing liver glycogen stores since glucose cannot be processed through the glycolytic pathway. (Vrana et al. (1978) Metabolism 27:885-888). This diet also impairs the ability of adipose and muscle tissue to use glucose for energy production (Bender and Thadini (1970) Nutr. Metab. 12:22-39; Kelsay et al. (1977) Am. J. Clin. Nutr. 30:2016-2022).

When fructose is used as an energy source, there is an elevation in the level of intermediates in glycolysis, but the cost of producing these intermediates is very high. (Hers (1952) Biochim. Biophys. Acta 8:416-423). As noted above, when fructose is consumed the majority of it enters the liver and is converted to fructose-1-phosphate. Thus, individuals who consume large amounts of fructose essentially as a glucose replacement are sequestering phosphate ions from the rest of the body in the form of fructose-1-phosphate via the action of fructokinase (FIG. 1; Woods et al. (1970) Biochem. J. 119:501-510). Because there is no phosphate ion in reserve the oxidative phosphorylation of ADP is inhibited resulting in a shortage of ATP in the liver. The conversion of glyceraldehyde to glyceraldehyde-3-phosphate by triokinase further depletes the phosphate pool to provide a substrate for glycolysis. When the phosphate pool becomes sufficiently low, there is a large production of AMP which is metabolized by the enzymes AMP deaminase and 5'-nucleotidase. (Mayes (1993) Am. J. Clin. Nutr. 58(Suppl):754S-765S). The metabolism of AMP, results in a rise in the levels of inosine, which eventually leads to the formation of large amounts of uric acid and the potential for hyperuricemia.

Hyperuricemia was first noticed in studies in which fructose was administered to normal as well as children with hereditary fructose intolerance. (Perheentup and Raivio (1967) Lancet 2:528-31). An increase in the incidence of hyperuricemia has also been detected when fructose is administered parenterally to both diabetics and to those suffering from gout. (Hallfrisch (1987) in: *Metabolic Effects of Dietary Fructose* (Reiser & Hallfrisch, eds), pp. 25-40, CRC Press, Boca Raton, Fla.). Even when healthy subjects consumed approximately 18% of their energy needs as fructose, many showed signs of hyperuricemia suggesting that average individuals are susceptible to the diminishing phosphate ion and ATP concentrations in the body. (Hallfrisch (1987) in: *Metabolic Effects of Dietary Fructose* (Reiser & Hallfrisch, eds), pp. 25-40, CRC Press, Boca Raton, Fla.).

Young males (ages 14-18) in particular may be the most at risk of hyperuricemia. According to the 1977-1978 U.S. Department of Agriculture Nationwide Food Consumption Survey, males in this age group consumed approximately 100 g per day of fructose primarily from soda. Since that time, fructose has also been introduced into the general food supply, particularly in the United States. Just two cans of soda alone contain approximately 50 g of fructose. It is estimated that average consumption of fructose has increased dramatically over the last 20 years from approximately 64 g per day to as much as 150 g per day for adolescent males. (Kanter (1998) "A dietary assessment of the US Food Supply: Comparing per capita food consumption with food guide pyramid serving recommendations," from the Food and Rural Economics Division, Economics Research Service, U.S. Department of Agriculture, Agricultural Economic Report no. 772; Elliott et al. (2002) Am. J. Clin. Nutr. 76:911-922). Thus, a whole generation of males is presently experiencing a lowering of their available pool of phosphate and ATP in the body. In addition to the increased risk of hyperuricemia, this has a significant effect on a number of processes in the body and actually may cause an inhibition of protein and nucleic acid synthesis leading to poor development in children, to an increase in the incidence of disease upon aging and to premature aging in general. (Maenpaa et al. (1968) Science 161: 1253-1254; Bode et al. (1973) Eur. J. Clin. Invest. 3:436-441).

One particular concern regarding the consumption of large amounts of sucrose and/or fructose is that fructose accelerates glycation or the non-enzymatic cross-linking of macromolecules such as nucleic acids, proteins and lipoproteins with sugars (the "Maillard Reaction"). Glycation was first reported by Monnier, who suggested that aging processes in the body might be contributed to by the Maillard reaction. (Monnier (1989) "Toward a Malliear reaction theory of aging. in: the *Malliard Reaction in Aging, Diabetes, and Nutrition*," (Baynes, J W & Monnier V M, eds.), pp. 1-22, Alan R. Liss, New York, N.Y.). In the Maillard reaction a sugar, such as glucose and fructose, reacts initially with an N-terminal amino group of a protein or nucleic acid to form a labile Schiff's base, which then undergoes rearrangement to form a more stable compound. Over time, the sugar moieties bound to the glycated proteins/amino acids are chemically modified to become molecular structures called Advanced Glycation Endproducts (AGEs). AGEs can interfere with the proper functioning of the proteins to which they are attached. Additionally, in the presence of reactive oxygen species (ROS), AGEs can covalently crosslink with adjacent protein strands. Thus, proteins literally conjugate to other macromolecules via covalent bond formation forming large, complexes that must then be cleared by the body.

In theory, both aldoses and ketoses can participate in Maillard reactions (Yaylayan and Huyghues (1994) Crit. Rev. Food Sci. 34:321-369), however glucose has been found to be much less reactive than fructose (Bunn and Higgins (1981) Science 213: 222-4; McPherson et al. (1988) Biochemistry 27:1901-1907). All molecules that have free amino groups may undergo the Malliard reaction in vivo. Usually, however, the ε-amino group of lysine is the principle reactant in glycation. Other amino acids such as arginine, histidine, tyrosine, tryptophan, serine, and threonine have also been implicated in the Malliard reaction between proteins and other macromolecules (Monnier (1989) "Toward a Malliear reaction theory of aging. In: the *Malliard Reaction in Aging, Diabetes, and Nutrition*," (Baynes, J W & Monnier V M, eds.), pp. 1-22, Alan R. Liss, New York, N.Y., 1989).

Diabetic patients are particularly susceptible to the effects of glycation if fructose is used as a substitute for glucose in their diets. As noted above, fructose is generally present in low concentration in the blood, but in diabetics an equal or greater concentration of fructose versus glucose is found in the corneal lens and nerves. (Jedziniak et al. (1981) Investig. Ophthalmol. Vis. Sci. 20:314-326; Mayhew et al. (1983) Diabetologia 24:13-15). This high concentration of fructose causes glycation between proteins in the lens resulting in blindness. (McPherson et al. (1988) Biochemistry 27:1901-1907). With the increase in fructose consumption over the last twenty years (Park and Yeltley (1993) Am. J. Clin. Nutr. 58

(supp):737S-747S), it is not surprising that blindness is the most prevalent microvascular complication associated with diabetes. (Jochmann and Hammes (2002) Z. Arztl. Fortbild. Qualitatssich. 96:167-174).

Of all the problems associated with high fructose intake, none matches the effect fructose has on lipid accumulation, lipogenesis and weight gain. In developing countries, low-fat, high-carbohydrate diets are prevalent owing to the extreme awareness regarding the dangers of fat and cholesterol in cardiovascular disease, endorsement of fructose as a substitute sweetener for diabetics and a lack of awareness of the dangers of fructose consumption. (Gerrits and Tsalikian (1993) Am. J. Clin. Nutr. 58(Supp.):796S-799S; Sonko et al. (1993) Acta Physiol. Scand. 147:99-108). This has led to a tremendous increase in fructose consumption correlating with increases in weight gain and obesity over the last thirty years for the reasons discussed below.

When simple sugars, particularly fructose, are ingested to the extent that they exceed the current energy demand, lipogenesis occurs. (Kazumi et al. (1997) Endocrinol. J. 44(2): 239-245; Noguchi and Tanaka (1995) Obes. Res. 3(Supp. 2):195S-198S). As noted above, lipogenesis includes the process of fatty acid synthesis and subsequent triglyceride synthesis. Because of the limited capacity of higher animals to store polysaccharides, when simple sugars, such as glucose and fructose, are ingested in excess of current energy needs and storage capacity they are converted into triacyl glycerols and stored in adipose or fat tissue. To understand how the composition described herein affects lipogenesis, one must first understand the pathways of lipid formation in the body. FIG. 1 illustrates the interplay between fructose and glucose in the formation of acyl glycerols, acetyl-CoA and ultimately very low density lipids (VLDL). There are two primary mechanisms by which fats are produced from carbohydrates. In the first, excess glucose is shunted toward fat production through the accumulation of acetyl CoA and de novo lipogenesis. With reference to FIG. 1, excess acetyl CoA is converted by acetyl CoA carboxylase to malonyl CoA, which is then converted to acyl CoA. Acyl CoA enters lipogenesis through an esterification reaction and is then converted to acyl glycerol by action of the enzyme glycerol-2-phosphate acyl transferase. The acyl glycerol in combination with cholesterol is then converted to very low-density lipids (VLDL). Insulin has a positive effect on this process driving de novo lipogenesis (Park et al. (1997) J. Lipid Res. 38:2529-2536).

Secondly, excess fructose is shunted toward fat production through the accumulation of dihydroxyacetone phosphate in excess of energy needs, which is converted to glycerol-3-phosphate (see FIG. 1). Glycerol-3-phosphate then undergoes esterification by glycerol-3-phosphate acyl transferase to yield acyl glycerol, which together with cholesterol produces VLDL. Due to the high energy cost of processing fructose through the glycolytic pathway, lipogenesis via VLDL production represents an energy savings to the body. Glycogen deposition from glucose (2.5 mol ATP/mole glucose) is also more efficient than that of fructose (3.5 mol ATP/mole fructose). (Tapp and Jequier (1993) Am. J. Clin. Nutr. 58:766S). As stated above, however, fructose metabolism has a negative effect on glycolysis and glycogen deposition, inhibiting gene and protein expression of key glycolytic enzymes, removing phosphate from the liver thereby decreasing ATP production, and finally decreasing general metabolic output in fructose induced obesity.

Several studies have indicated that fructose is more lipogenic than glucose. Rats fed continuous high amounts of fructose developed increased concentrations of VLDL triglycerides in their blood. (Herman et al. (1970) Fed. Proc. 29:1302-1307; Steiner et al. (1984) Am. J. Physiol. 246: E187-E192; Kazumi et al. (1986) Am. J. Physiol. 250:E325-E330). When fructose was ingested, there was an immediate formation of high levels of plasma triglycerides, as well as, an increase in the rate of glycerol and fatty acid formation. (Reiser (1987) "Lipogenesis and blood lipids," in: *Metabolic effects of dietary fructose*, (Reiser S & Hallfrisch J, eds.), pp. 83-111, CRC Press, Boca Raton, Fla.; Hallfrisch (1990) FASEB J. 4:2652-2660). Chronic consumption of fructose also increased the levels of mRNA or enzymes involved in lipogenesis such as fatty acid synthase (Bruckdorfer et al. (1972) Biochem. J. 129:439-446) and glycerol-3-phosphate dehydrogenase (Borrebach et al. (1976) Circ. Res. 38:1-21; Declerecq et al. (1982) Biochem. J. 204:247-256). Conversely, chronic diets of fructose decreased the activity of a number of key glycolytic enzymes including ATP-citrate lyase (Moser and Berdamier (1974) J. Nutr. 104:687-94; Shafir et al. (1975) Isr. J. Med. Sci. 11: 1150-1154; Winder et al. (1975) Proc. Soc. Exp. Biol. Med. 148:1150-1154), acetyl-CoA carboxylase (Bruckdorfer et al. (1972) Biochem. J. 129: 439-446; Winder et al. (1975) Proc. Soc. Exp. Biol. Med. 148:1150-1154; Waterman et al. (1975) Proc. Soc. Exp. Biol. Med. 150:220-225), glucose-6-phosphate dehydrogenase, NADP malate dehydrogenase and pyruvate kinase. The ingestion of starch, however, enhanced the activity of these enzymes. (Vrana and Fabry (1983) World Res. Nutr. Diet 42:56-101). In particular, induction of glycerol-3-phosphate dehydrogenase leads to an increase in VLDL content in the liver by converting dihydroxyacetone phosphate to glycerol-3-phosphate (see FIG. 1).

Lipogenesis has been shown to increase in the livers of rats fed chronic fructose (Christophe and Mayer (1968) Am. J. Physiol. 197:55-59) or sucrose diets (Fabry et al. (1968) Nutr. Dieta 10:81-90; Tepperman and Tepperman (1970) Fed. Proc. 29:1284-1293). Rats fed high fructose diets also showed increased lipid content and large increases in organ weight compared to animals on standard starch or glucose supplemented diets. (Wapnir and Devas (1995) Am. J. Clin. Nutr. 61:105-110). The kidneys were affected to a lesser extent in animals on high fructose diets. Heart and testes weights were unaffected. The addition of high fat to a high fructose diet added minimally to the overall liver weight in these studies suggesting that fructose induced lipogenesis was the primary pathway by which fat was produced. (Wapnir and Devas (1995) Am. J. Clin. Nutr. 61:105-110).

Most of the studies performed to date have been done in rats where diet can be closely controlled. There is mounting evidence, however, that increased fructose consumption is taking a toll on humans. Several studies have shown that fructose has a definite effect on weight gain in men and women. For example, when 14 middle-aged men, four with diabetes, supplemented their diets with an additional 50-60 g of fructose per day or roughly the equivalent of two cans of soda sweetened with high fructose corn syrup, they all exhibited a net weight gain. (Anderson et al. (1989) Diabetes Care 12:337-344). In another study in which overweight individuals were compared consuming either artificial sweetener or sucrose (50% fructose) as 28% of their of their energy needs, the individuals taking sucrose supplements showed increases in body weight, fat mass and blood pressure over a 10 week period. (Atrup et al. (2002) Am. J. Clin. Nutr. 75(Suppl):405S (abstract)). Further, Raben et al. showed that individuals that were given starch reduced their body mass over a 14 day period, in contrast to individuals given sucrose (50% fructose) who showed no change in weight. (Raben et al. (1997) Int. J. Obes. Relat. Metab. Disord. 21:846-859). These observations are all in line with studies done by Schwarz et al., which show an increase in fructose-induced lipogenesis in both lean and obese subjects. (Schwarz et al. (1995) J. Clin. Invest. 96:2735-2743).

Certain pro-inflammatory markers are associated with weight gain and obesity. Among these are TNFα, IL-6 and CRP. TNFα is expressed and secreted by adipocytes and shows a direct correlation with obesity and BMI, but not necessarily with insulin insensitivity and hyperinsulinemia (Hotamisligil et al. (1993) Science 259:87-91; Ronnemaa et al. (2000) J. Clin. Endocrinol. Metab. 85:2728-2732; Berberoglu (2001) J. Pediatr. Endocrinol. Metab. 14:543-547).

Body Mass Index (BMI) is a measure of body fat based on height and weight. BMI is used as a measure of overall obesity and is one of many factors related to the potential for developing a chronic disease (such as heart disease, cancer or diabetes). Other important factors in assessing ones risk for developing a chronic disease include diet, physical activity, waist circumference, blood pressure, blood sugar levels, cholesterol levels and family history of disease. BMI is calculated as follows:

$$BMI = \left(\frac{\text{Weight in pounds (lbs)}}{(\text{Height in inches (in)})^2}\right) \times 703$$

Individuals are considered overweight if their BMI is between 25-29.9 kg/m$^2$ and obese if their BMI≧30 kg/m$^2$. Individuals whose BMI is <25 kg/m$^2$ are considered to be normal weight.

There are three types of adiposity in the body—subcutaneous, visceral and organ. (Cinti (2000) Eat Weight Disord. 5:132-142). Liver (organ) adiposity has been shown to be highly associated with fructose consumption (Wapnir and Devas (1995) Am. J. Clin. Nutr. 61:105-110). Visceral adiposity, on the other hand, is associated with the intake of a variety of fat and carbohydrate sources, including fructose/sucrose. (Tarui et al. (1991) Int. J. Obes. 2(Suppl): 1-8; Keno et al. (1991) Int. J. Obes. 15:205-211). The greater the amount of visceral adiposity, the greater the amount of TNFα generated by the body. (Tsigos et al. (1999) Metabolism 48:1332-5; Vgontzas et al. (2000) J. Clin. Endorcrinol. Metab. 85:1151-1158). High sucrose/fructose diets have been found to increase visceral adiposity.

TNFα induces secretion of IL-6 from adipose tissue which causes glucorticoid induced lipolysis thereby releasing increased concentrations of circulating nonesterified fatty acids that can serve as an additional pool for de novo fat synthesis. (Patton et al. (1986) Proc. Natl. Acad. Sci. USA 83:8313-8317; Fried et al. (1998) Endocrinol. Metab. 83:847-850). In high fructose fed LDL-receptor deficient mice, atherosclerotic lesions contained high levels of TNFα that induced transcription factors promoting gene expression of proteins that induce even greater lesion formation (Goetze et al. (2001) Atherosclerosis 159:93-101).

Acute phase represents a state of injury or inflammation in which IL-6 induces gene and protein expression of specific inflammatory proteins, such as CRP and fibrinogen (Heinrich et al. (1990) Biochem. J. 265:621-636). No other cytokine performs this function in the acute phase. Although there was known to be a strong correlation between increased BMI and serum fibrinogen concentrations (Krobot et al. (1991) Arterioscler. Thromb. 12:780-788), there was no clear association with IL-6 until it was discovered that abdominal fat cells produce and secrete IL-6 (Mohamed-Ali et al. (1997) J. Clin. Endocrinol. Metab. 82:4196-4200). Thus, there is a direct correlation between IL-6 levels in the body, BMI, and visceral adiposity.

The secondary effects of IL-6 production may be even more damaging than those noted above. IL-6 secretion from visceral adipocytes is taken up primarily by the portal vein, thus acting primarily on hepatocytes. Like TNFα, IL-6 also promotes lipolysis in the liver, but it especially increases fibrinogen gene expression leading to high concentrations of fibrogenin in the blood and an increased incidence of cardiovascular disease. (McCarty (1999) Medical Hypotheses 52:465-477).

Associated with its gene expression activity is IL-6's effect on increasing CRP levels in circulation. IL-6 regulates the hepatic synthesis of CRP (Heinrich et al. (1990) Biochem. J. 265:621-636; Bataille and Klein (1992) Arthritis Rheum. 35:982-983). Since there is a correlation between increased BMI and TNFα and IL-6 concentrations, researchers looked for a correlation with respect to CRP. It was discovered that there is a direct correlation between CRP serum concentrations and BMI. (Visser et al. (1999) JAMA 282:2131-2135). In fact, there is almost a linear relationship between BMI and CRP concentration.

In comparison to TNFα and IL-6, an even stronger correlation was found between visceral adiposity and CRP concentrations, (Forouhi et al. (2001) Int. J. Obes. Relat. Metab. Disord. 25:1327-1331) so much so that it could be the primary predictor in endothelial function in the brachial artery during acute phase cardiovascular disease (Brooks et al. (2001) Am. J. Cardiol. 88:1264-9). Excessive fructose and sucrose intake would most certainly lead to an increase in CRP due to increased secretion of TNFα inducing high levels of IL-6 which then induces expression of CRP. This cytokine cascade, caused initially by an up-regulation in fructose-induced lipogenesis in the liver is responsible for the primary protein determinants in obesity, cardiovascular disease, diabetes as well as many other diseases. (McCarty (1999) Medical Hypotheses 52:465-477). Reduction of fructose and sugar-induced weight gain is vital in preventing these inflammation based disease states.

"Starch blockers" are compounds derived from plants that partially inhibit the action of α-amylase, thus causing starch to pass through the gut underutilized as a source of glucose. In particular, phaseolamin an extract isolated from kidney beans has been found to be effective in blocking carbohydrate breakdown via inhibition of α-amylase. (Marshall and Lauda (1975) J. Biol. Chem. 250:8030-8037). A number of "starch blockers" isolated from a variety of plant sources are currently commercially available. A comprehensive search of the literature for plants and plant extracts that effect sugar-induced weight gain however produced only one result. Bofutsusho-san (BOF), a traditional Chinese medicine, inhibited triglyeride synthesis in the liver and enhanced lipolysis in adipocytes. (Morimoto et al. (2001) Nippon Yakurigaku Zasshi 117:77-86). Analysis of this extract, however, revealed that it contained ephedrine and d-pseudoephedrine which inhibit phosphodiesterase (PDE) activity in adipocytes, thus accounting for its effect on inhibition of weight gain. (Yoshida et al. (1995) Int. J. Obes. Relat. Metab. Disord. 19:717-722). Mu Huang, another well known plant extract used for weight loss, also contains ephedra, an ephedrine like substance. (Boozer et al. (2002) Int. J. Obes. Relat. Metab. Disord. 26:593-604; Boozer et al. (2001) Int. J. Obes. Relat. Metab. Disord. 25:316-324). Though several short-term clinical studies have shown Mu Huang to be safe in combination with caffeine and guarana, recent reports have suggested that ephedra containing weight loss preparations have severe cardiac side effects.

The composition of matter described herein contains no α-amylase inhibitors, which effect starch breakdown and no ephedra, ephedrine, or pseudoephedrine, which effect sugar metabolism and weight gain. This extract decreases weight gain in high sugar diets via reduction in fructose utilization, reduces pro-inflammatory cytokines associated with obesity, and may aid in weight loss.

Flavonoids or bioflavonoids are a widely distributed group of natural products, which have been reported to have antibacterial, anti-inflammatory, antiallergic, antimutagenic, antiviral, antineoplastic, anti-thrombic and vasodilatory activity. The structural unit common to this group of compounds includes two benzene rings on either side of a 3-carbon ring as illustrated by the following general structural formula:

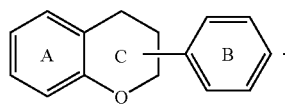

Various combinations of hydroxyl groups, sugars, oxygen and methyl groups attached to this general three ring structure create the various classes of flavonoids, which include flavanols, flavones, flavan-3-ols (catechins), anthocyanins and isoflavones.

Free-B-Ring flavones and flavonols are a specific class of flavonoids, which have no substituent groups on the aromatic B ring, as illustrated by the following general structure:

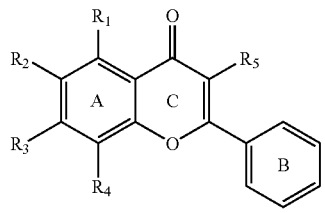

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

Though flavonoids are a widely distributed group of natural products, Free-B-Ring flavonoids are relatively rare. Out of a total 9396 flavonoids synthesized or isolated from natural sources, only 231 Free-B-Ring flavonoids are known. (The Combined Chemical Dictionary, Chapman & Hall/CRC, Version 5:1 June 2001). Free-B-Ring flavonoids have been reported to have diverse biological activity. For example, galangin (3,5,7-trihydroxyflavone) acts as anti-oxidant and free radical scavenger and is believed to be a promising candidate for anti-genotoxicity and cancer chemoprevention. (Heo et al. (2001) Mutat. Res. 488(2):135-150). It is an inhibitor of tyrosinase monophenolase (Kubo et al. (2000) Bioorg. Med. Chem. 8(7):1749-1755), an inhibitor of rabbit heart carbonyl reductase (Imamura et al. (2000) J. Biochem. 127 (4):653-658), has antimicrobial activity (Afolayan and Meyer (1997) Ethnopharmacol. 57(3):177-181) and antiviral activity (Meyer et al. (1997) J. Ethnopharmacol. 56(2):165-169). Baicalein and galangin, two other Free-B-Ring flavonoids, have antiproliferative activity against human breast cancer cells. (So et al. (1997) Cancer Lett. 112(2):127-133).

Typically, flavonoids have been tested for activity randomly based upon their availability. Occasionally, the requirement of substitution on the B-ring has been emphasized for specific biological activity, such as the B-ring substitution required for high affinity binding to p-glycoprotein (Boumendjel et al. (2001) Bioorg. Med. Chem. Lett. 11(1): 75-77); cardiotonic effect (Itoigawa et al. (1999) J. Ethnopharmacol. 65(3): 267-272), protective effect on endothelial cells against linoleic acid hydroperoxide-induced toxicity (Kaneko and Baba (1999) Biosci Biotechnol. Biochem 63(2): 323-328), COX-1 inhibitory activity (Wang (2000) Phytomedicine 7:15-19); and prostaglandin endoperoxide synthase activity (Kalkbrenner et al. (1992) Pharmacology 44(1): 1-12). Only a few publications have mentioned the significance of the unsubstituted B-ring of the Free-B-Ring flavonoids. One example, is the use of 2-phenyl flavones, which inhibit NAD(P)H quinone acceptor oxidoreductase, as potential anticoagulants. (Chen et al. (2001) Biochem. Pharmacol. 61(11):1417-1427).

The Chinese medicinal plant, *Scutellaria baicalensis* contains significant amounts of Free-B-Ring flavonoids, including baicalein, baicalin, wogonin and baicalenoside. Traditionally, this plant has been used to treat a number of conditions including clearing away heat, purging fire, dampness-warm and summer fever syndromes; polydipsia resulting from high fever; carbuncle, sores and other pyogenic skin infections; upper respiratory infections, such as acute tonsillitis, laryngopharyngitis and scarlet fever; viral hepatitis; nephritis; pelvitis; dysentery; hematemesis and epistaxis. This plant has also been used traditionally to prevent miscarriage (*Encyclopedia of Chinese Traditional Medicine* Shang-Hai Science and Technology Press, ShangHai, China, 1998). Clinically *Scutellaria* is now used to treat conditions such as pediatric pneumonia, pediatric bacterial diarrhea, viral hepatitis, acute gallbladder inflammation, hypertension, topical acute inflammation, resulting from cuts and surgery, bronchial asthma and upper respiratory infections (Encyclopedia of Chinese Traditional Medicine, ShangHai Science and Technology Press, ShangHai, China, 1998). The pharmacological efficacy of *Scutellaria* roots for treating bronchial asthma is reportedly related to the presence of Free-B-Ring flavonoids and their suppression of eotaxin associated recruitment of eosinophils. (Nakajima et al. (2001) Planta Med. 67(2):132-135).

To date, a number of naturally occurring Free-B-Ring flavonoids have been commercialized for varying uses. For example, liposome formulations of *Scutellaria* extracts have been utilized for skin care (U.S. Pat. Nos. 5,643,598; 5,443, 983). Baicalin has been used for preventing cancer, due to its inhibitory effects on oncogenes (U.S. Pat. No. 6,290,995). Baicalin and other compounds have been used as antiviral, antibacterial and immunomodulating agents (U.S. Pat. No. 6,083,921) and as natural anti-oxidants (Poland Pub. No. 9,849,256). Chrysin has been used for its anxiety reducing properties (U.S. Pat. No. 5,756,538). Anti-inflammatory flavonoids are used for the control and treatment of anorectal and colonic diseases (U.S. Pat. No. 5,858,371), and inhibition of lipoxygenase (U.S. Pat. No. 6,217,875). These compounds are also formulated with glucosamine collagen and other ingredients for repair and maintenance of connective tissue (Bath, U.S. Pat. No. 6,333,304). Flavonoid esters constitute active ingredients in cosmetic compositions (U.S. Pat. No. 6,235,294). U.S. application Ser. No. 10/091,362, filed Mar. 1, 2002, entitled "Identification of Free-B-Ring Flavonoids as Potent Cox-2 Inhibitors," discloses a method for inhibiting the cyclooxygenase enzyme COX-2 by administering a composition comprising a Free-B-Ring flavonoid or a composition containing a mixture of Free-B-Ring flavonoids to a host in need thereof. This is the first report of a link between Free-B-Ring flavonoids and COX-2 inhibitory activity. This application is incorporated herein by reference in its entirety.

Flavans include compounds illustrated by the following general structure:

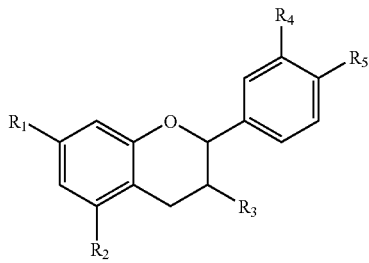

wherein $R_1$, $R_2$, $R_3$, $R_4$ and $R_5$ are independently selected from the group consisting of —H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, and carbonate, etc.

Catechin is a flavan, found primarily in green tea, having the following structure.

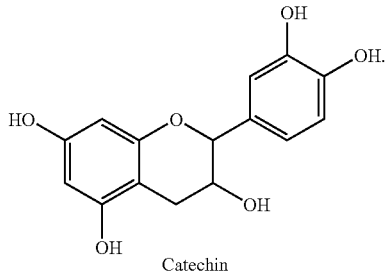

Catechin

Catechin works both alone and in conjunction with other flavonoids found in tea, and has both antiviral and antioxidant activity. Catechin has been shown to be effective in the treatment of viral hepatitis. It also appears to prevent oxidative damage to the heart, kidney, lungs and spleen. Catechin has also been shown to inhibit the growth of stomach cancer cells.

Catechin and its derivatives from various plant sources, especially from green tea leaves, have been used in the treatment of HPV infected Condyloma acuminata (Cheng, U.S. Pat. No. 5,795,911) and hyperplasia caused by papilloma virus (Cheng, U.S. Pat. Nos. 5,968,973 and 6,197,808). Catechin and its derivatives have also been used topically to inhibit angiogenesis in mammalian tissue, such as skin cancer, psoriasis, spider veins or under eye circles (Anderson, U.S. Pat. No. 6,248,341), against UVB-induced tumorigenesis on mice (Agarwal et al. (1993) Photochem. Photobiol. 58:695-700), for inhibiting nitric oxide synthase at the level of gene expression and enzyme activity (Chan, U.S. Pat. No. 5,922,756) and as a hair-growing agent (Takahashi, U.S. Pat. No. 6,126,940). Catechin based compositions have also been formulated with other extracts and vitamins for treatment of acne (Murad U.S. Pat. No. 5,962,517), hardening the tissue of digestive organs (Shi, U.S. Pat. No. 5,470,589) and for inhibiting 5 alpha-reductase activity in treating androgenic disorder related diseases and cancers (Liao, U.S. Pat. No. 5,605,929). Green tea extract has been formulated with seven other plant extracts for reducing inflammation by inhibiting the COX-2 enzyme, without identification of any of the specific active components (Newmark, U.S. Pat. No. 6,264,995).

The flavans, quercetin and fisetin, were shown to stimulate PDE activity in adipose tissue as opposed to inhibition of activity in stimulating lipolysis. (Kuppusamy and Das (1994) Biochem. Pharmacol. 47:521-529). Quercetin and fisetin stimulated PDE activity in a dose dependent manner, both in the presence and absence of epinephrine, causing cellular accumulation of cyclic AMP. Additionally, their action was not potentiated by the addition of theophylline, a known lipolytic agent, but rather their action was inhibited by the addition of a specific β-adrenocepter agonist, isoprterenol, suggesting that quercetin and fisetin act synergistically with epinephrine by binding to the β-adrenocepter. Catechin also stimulated PDE activity, but not in the presence of epinephrine suggesting that it weakly binds the β-adrenocepter. (Kuppusamy and Das (1992) Biochem. Pharmacol. 44:1307-1315). Further, in studies in mice over a one month period, green tea catechins caused increases in acyl CoA oxidase, medium chain acyl CoA dehydrogenase, as well as β-oxidation activity in the liver, thus increasing lipid catabolism. (Murase et al. (2002) Int. J. Obes. Relat. Metab. Disord. 26:1459-1464).

Catechin's effect on fructose-induced obesity is not known. There is also no evidence that baicalein, baicalin, or wogonin effect fructose metabolism. Yet an extract containing a combination of both herbs does alter fructose metabolism as detailed below.

Acacia is a genus of leguminous trees and shrubs. The genus Acacia includes more than 1000 species belonging to the family of Leguminosae and the subfamily of Mimosoideae. Acacias are distributed worldwide in tropical and subtropical areas of Central and South America, Africa, parts of Asia, as well as, Australia, which has the largest number of endemic species. Acacias occur primarily in dry and arid regions, where the forests are often in the nature of open thorny shrubs. The genus Acacia is divided into 3 subgenera based mainly on the leaf morphology—Acacia, Aculiferum and Heterophyllum. Based on the nature of the leaves of mature trees, however, the genus Acacia can be divided into two "popular" groups: the typical bipinnate leaved species and the phyllodenous species. A phyllode is a modified petiole expanded into a leaflike structure with no leaflets, an adaptation to xerophytic conditions.

*Acacias* are very important economically, providing a source of tannins, gums, timber, fuel and fodder. Tannins, which are isolated primarily from bark, are used extensively for tanning hides and skins. Some *Acacia* barks are also used for flavoring local spirits. Some indigenous species like *A. sinuata* also yield saponins, which are any of various plant glucosides that form soapy lathers when mixed and agitated with water. Saponins are used in detergents, foaming agents and emulsifiers. The flowers of some *Acacia* species are fragrant and used to make perfume. For example, cassie perfume is obtained from *A. ferrugenea*. The heartwood of many *Acacias* is used for making agricultural implements and also provides a source of firewood. *Acacia* gums find extensive use in medicine and confectionary and as sizing and finishing materials in the textile industry. Lac insects can be grown on several species, including *A. nilotica* and *A. catechu*. Some species have been used for forestation of wastelands, including *A. nilotica*, which can withstand some water inundation and a few such areas have become bird sanctuaries.

To date, approximately 330 compounds have been isolated from various *Acacia* species. Flavonoids, a type of water-soluble plant pigments, are the major class of compounds isolated from *Acacias*. Approximately 180 different flavonoids have been identified, 111 of which are flavans. Terpenoids are second largest class of compounds isolated from species of the *Acacia* genus, with 48 compounds having been identified. Other classes of compounds isolated from *Acacia* include, alkaloids (28), amino acids/peptides (20), tannins (16), carbohydrates (15), oxygen heterocycles (15) and aliphatic compounds (10). (Buckingham, *The Combined Chemical Dictionary*, Chapman & Hall CRC, version 5:2, December 2001).

Phenolic compounds, particularly flavans are found in moderate to high concentrations in all *Acacia* species. (Abdulrazak et al. (2000) Journal of Animal Sciences. 13:935-940). Historically, most of the plants and extracts of the *Acacia* genus have been utilized as astringents to treat gastrointestinal disorders, diarrhea and indigestion and to stop bleeding. (Vautrin (1996) Universite Bourgogne (France) European abstract 58-01C:177; Saleem et al. (1998) Hamdard Midicus. 41:63-67). The bark and pods of *A. arabica Willd*. contain large quantities of tannins and have been utilized as astringents and expectorants. (Nadkarni (1996) India Materia Medica, Bombay Popular Prakashan, pp. 9-17). Diarylpropanol derivatives, isolated from stem bark of *A. tortilis* from Somalia, have been reported to have smooth muscle relaxing effects. (Hagos et al. (1987) Planta Medica. 53:27-31, 1987). It has also been reported that terpenoid saponins isolated from *A. victoriae* have an inhibitory effect on dimethylbenz(a)anthracene-induced murine skin carcinogenesis (Hanausek et al. (2000) Proceedings American Association for Cancer Research Annual Meeting 41:663) and induce apotosis (Haridas et al. (2000) 3Proceedings American Association for Cancer Research Annual Meeting. 41:600). Plant extracts from *A. nilotica* have been reported to have spasmogenic, vasoconstrictor and anti-hypertensive activity (Amos et al. (1999) Phytotherapy Research 13:683-685; Gilani et al. (1999) Phytotherapy Research. 13:665-669), and antiplatelet aggregatory activity (Shah et al. (1997) General Pharmacology. 29:251-255). Anti-inflammatory activity has been reported for *A. nilotica*. It was speculated that flavonoids, polysaccharides and organic acids were potential active components. (Dafallah and Al-Mustafa (1996) American Journal of Chinese Medicine. 24:263-269). U.S. application Ser. No. 10/104,477, filed Mar. 22, 2002, entitled "Isolation of a Dual Cox-2 and 5-Lipoxygenase Inhibitor from *Acacia*," which is incorporated herein by reference in its entirety, discloses a method for the simultaneous dual inhibition of the cyclooxygenase COX-2 and 5-lipoxygenase (5-LO) enzymes by administering a composition comprising a flavan or a mixture of flavans isolated from the *Acacia* genus of plants.

SUMMARY OF THE INVENTION

The present invention includes methods that are effective in inhibiting sugar induced weight gain and sugar induced obesity. The methods for inhibiting sugar induced weight gain and inhibiting sugar induced obesity are comprised of administering a composition comprising a mixture of Free-B-Ring flavonoids and flavans synthesized and/or isolated from a single plant or multiple plants to a host in need thereof (this composition of matter is also referred to herein by the tradename DIAFIN™). The ratio of Free-B-Ring flavonoids to flavans can be in the range of 99.9:0.1 Free-B-Ring flavonoids:flavans to 0.1:99.9 Free-B-Ring flavonoids:flavans. In a preferred embodiment of this invention the ratio of Free-B-Ring flavonoids:flavans in the composition of matter is 80:20. In a preferred embodiment the Free-B-Ring flavonoids are isolated from a plant or plants in the *Scutellaria* genus of plants and the flavans are isolated from a plant or plants in the *Acacia* genus of plants.

The present invention also includes a method for the prevention and treatment of other sugar-induced diseases and conditions. The method for preventing and treating sugar-induced diseases and conditions is comprised of administering to a host in need thereof an effective amount of a composition comprising a mixture of Free-B-Ring flavonoids and flavans synthesized and/or isolated from a single plant or multiple plants and a pharmaceutically acceptable carrier. The ratio of Free-B-Ring flavonoids to flavans can be in the range of 99.9:0.1 Free-B-Ring flavonoids:flavans to 0.1:99.9 Free-B-Ring flavonoids:flavans. In a preferred embodiment of this invention the ratio of Free-B-Ring flavonoids:flavans in the composition of matter is 80:20. In a preferred embodiment the Free-B-Ring flavonoids are isolated from a plant or plants in the *Scutellaria* genus of plants and the flavans are isolated from a plant or plants in the *Acacia* genus of plants.

The present invention further includes methods for the specific inhibition of a key enzyme in the fructose catalytic and glycolytic pathways, namely the inhibition of a specific fructose 1-phosphate aldolase. With reference to FIG. 1, this inhibits the conversion of fructose 1-phosphate to glyceraldehyde and dihydroxy acetone-phosphate by aldolase. This specific inhibition prevents the conversion of dihydroxy acetone-phosphate to glycerol-3-phosphate and then acyl glycerol resulting ultimately in the production of VLDL.

The present invention also includes methods for genomic reduction of the transcription factor NFκB which induces production of TNFα and IL-6. TNFα and IL-6 are prime markers for obesity and other inflammatory diseases. The method for reduction of NFκB and subsequently TNFα and IL-6, is comprised of administering to a host in need thereof an effective amount of a composition comprising a mixture of Free-B-Ring flavonoids and flavans synthesized and/or isolated from a single plant or multiple plants. The ratio of Free-B-Ring flavonoids to flavans can be in the range of 99.9:0.1 Free-B-Ring flavonoids:flavans to 0.1:99.9 Free-B-Ring flavonoids:flavans. In a preferred embodiment of this invention the ratio of Free-B-Ring flavonoids:flavans in the composition of matter is 80:20. In a preferred embodiment the Free-B-Ring flavonoids are isolated from a plant or plants in the *Scutellaria* genus of plants and the flavans are isolated from a plant or plants in the *Acacia* genus of plants.

The Free-B-Ring flavonoids, also referred to herein as Free-B-Ring flavones and Free-B-Ring flavonols, that can be used in accordance with the following invention include compounds illustrated by the following general structure:

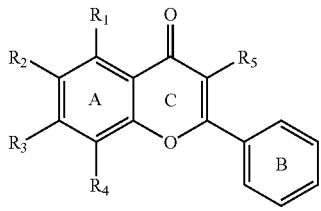

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The flavans that can be used in accordance with the following invention include compounds illustrated by the following general structure:

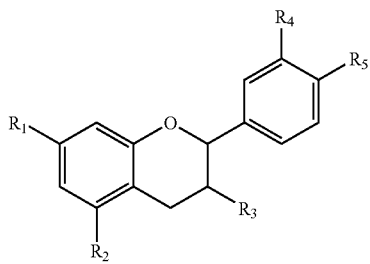

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The method of this invention can be used to treat and prevent a number of obesity associated diseases and conditions including, but not limited to hyperlipidemia, high cholesterol, arteriosclerosis, atherosclerosis, syndrome X (metabolic syndrome), systemic inflammation conditions caused by sugar-induced obesity and diabetes, and hypertension.

The Free-B-Ring flavonoids of this invention may be obtained by synthetic methods or extracted from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*.

The flavans of this invention may be obtained from a plant or plants selected from the genus of *Acacia*. In a preferred embodiment, the plant is selected from the group consisting of *Acacia catechu* (*A. catechu*), *A. concinna, A. farnesiana, A. Senegal, A. speciosa, A. arabica, A. caesia, A. pennata, A. sinuata. A. mearnsii, A. picnantha, A. dealbata, A. auriculiformis, A. holoserecia* and *A. mangium*.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of a mixture of Free-B-Ring flavonoids and flavans synthesized and/or isolated from a single plant or multiple plants.

It is to be understood that both the foregoing general description and the following detailed description are exemplary and explanatory only and are not restrictive of the invention as claimed.

Figure 5:
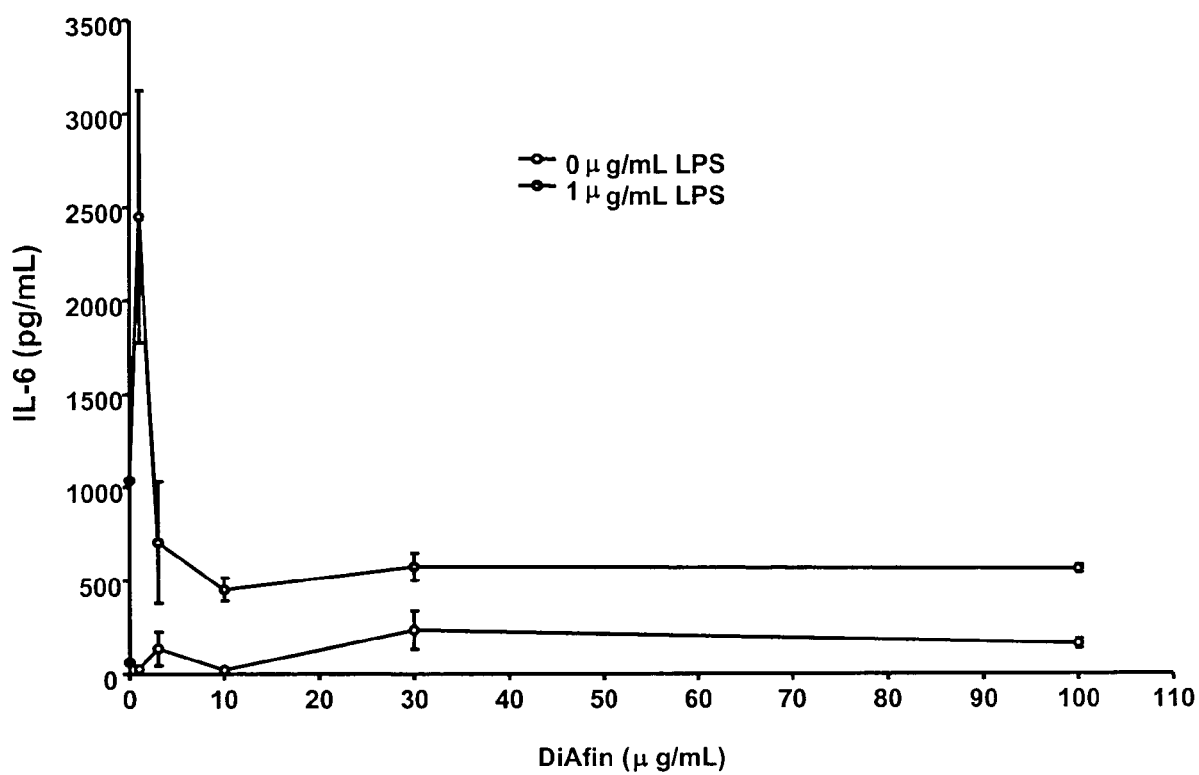

FIG. 5 depicts the effect of a mixture of Free-B-Ring flavonoids and flavans (80:20) on the lipopolysaccharide (LPS)-induced level of IL-6 in peripheal blood monocytes (PBMC) following exposure to the lipopolysaccharide in conjunction with different concentrations of the Free-B-Ring flavonoid and flavan mixture for six hours. The level of IL-6 is expressed in pg/mL. The standard deviation is shown for each data point.

Figure 6:
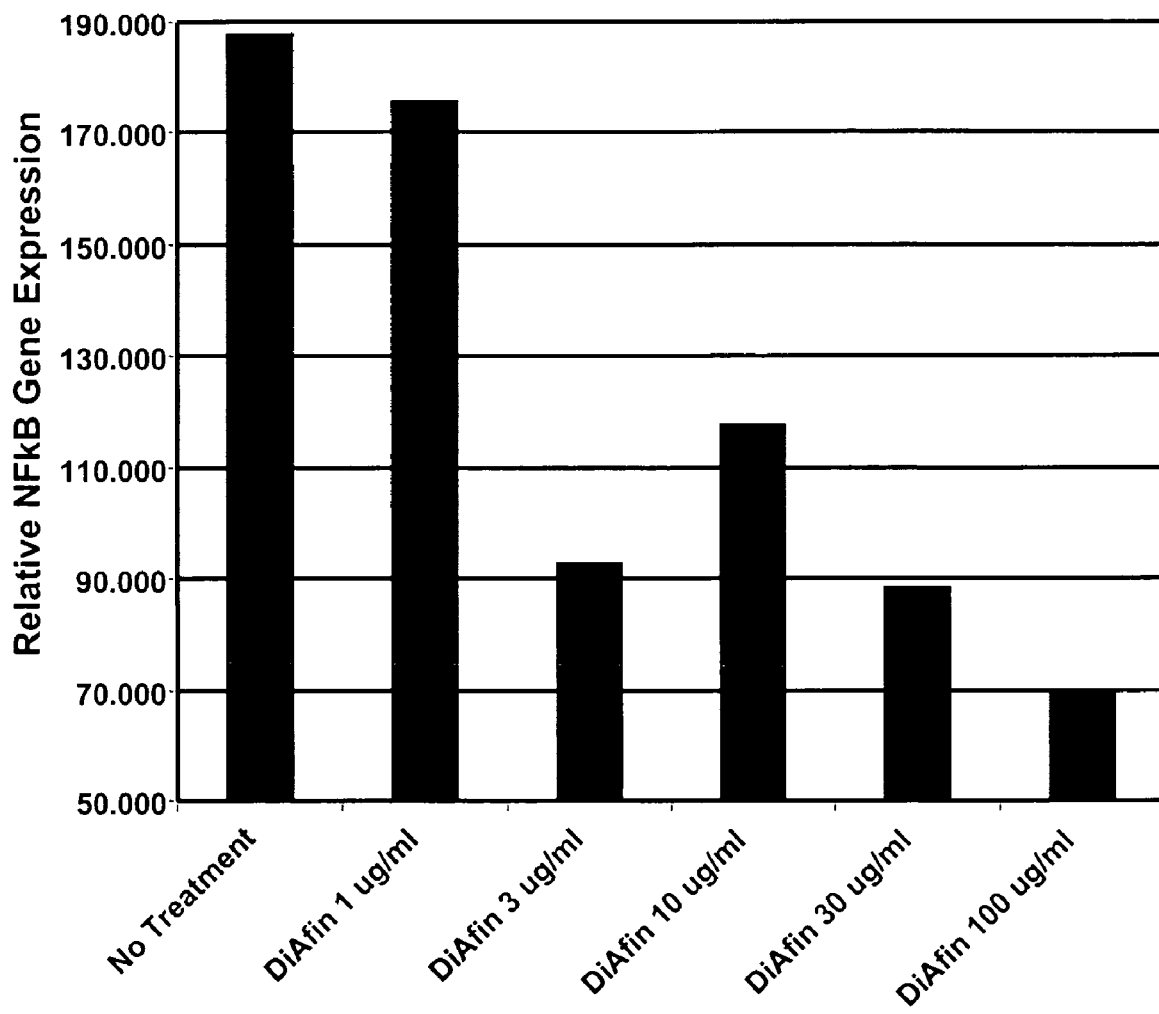

FIG. 6 depicts graphically the relative degree of inhibition of NFκB gene expression by a mixture of Free-B-Ring flavonoids and flavans. Relative gene expression was measured in the presence of 0 to 100 μg/mL of extract.

Figure 7:
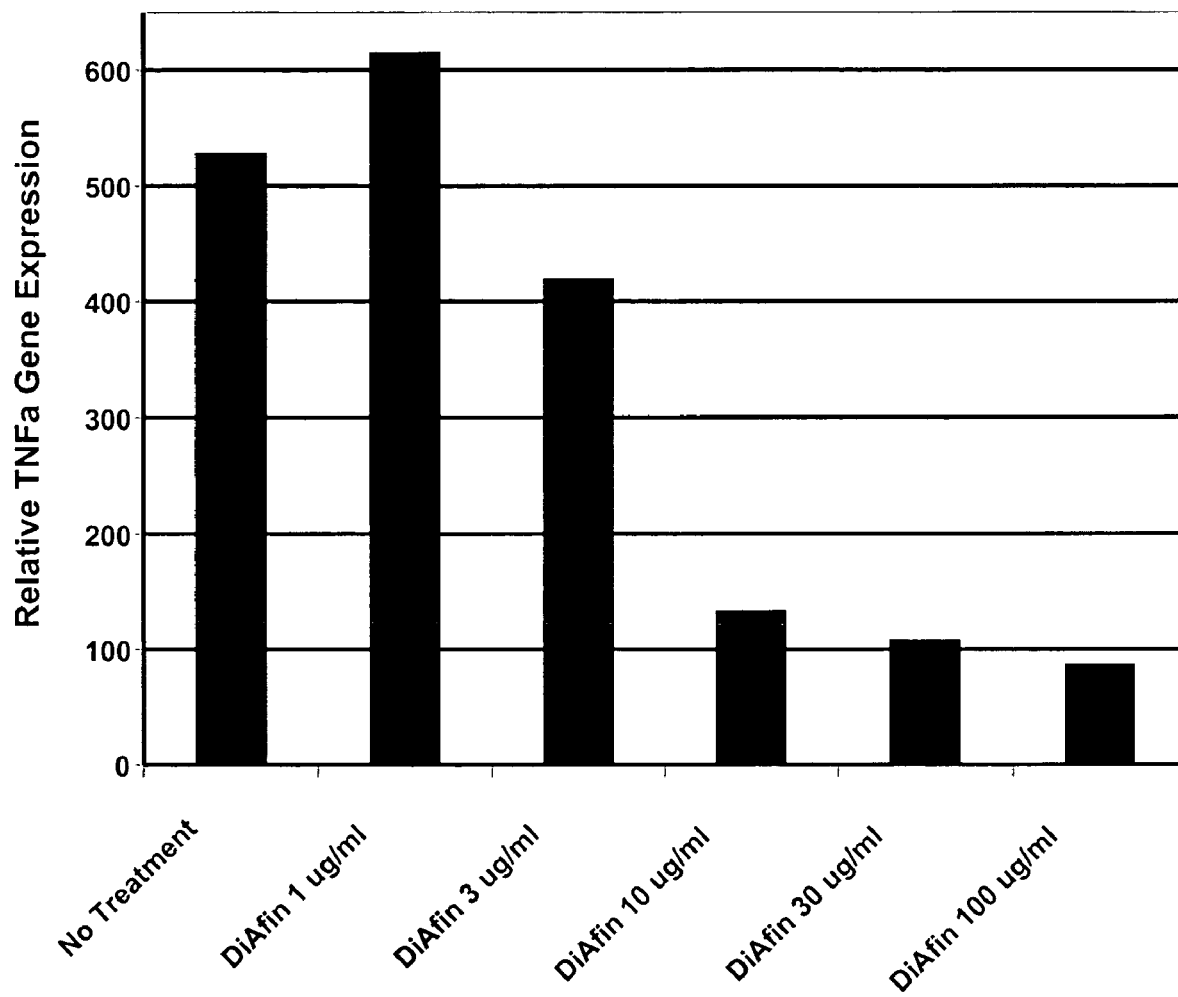

FIG. 7 depicts graphically the relative degree of inhibition of TNFα gene expression by a mixture of Free-B-Ring flavonoids and flavans. Relative gene expression was measured in the presence of 0 to 100 μg/mL of extract.

Figure 8:
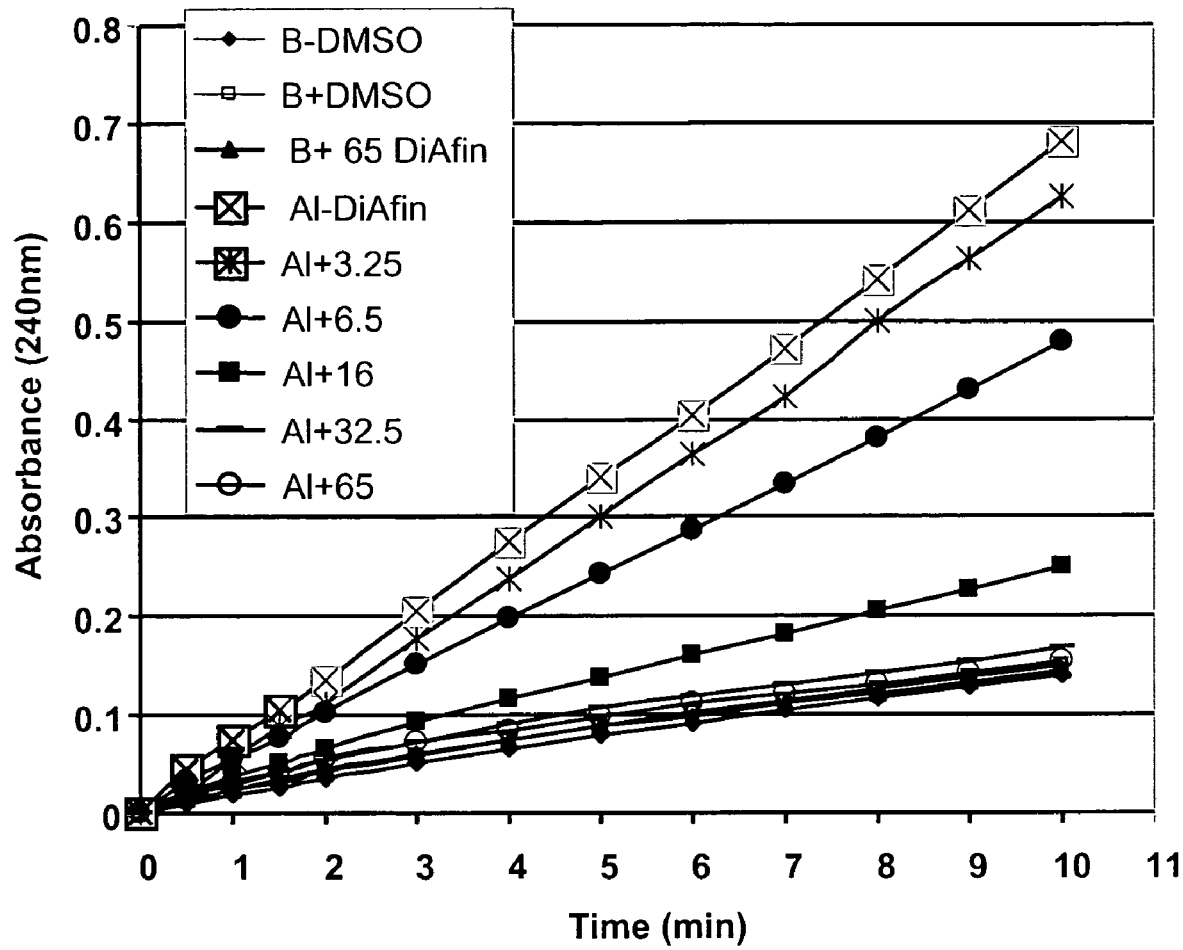

FIG. 8 illustrates graphically the effect of a mixture of Free-B-Ring flavonoids and flavans have on the function of a fructose 1-phosphate specific aldolase, which catalyzes the conversion of fructose 1-phosphate to glyceraldehyde and dihydroxyacetone phosphate. Dose specific inhibition of this key enzyme is shown over a period of 10 minutes.

Figure 9:
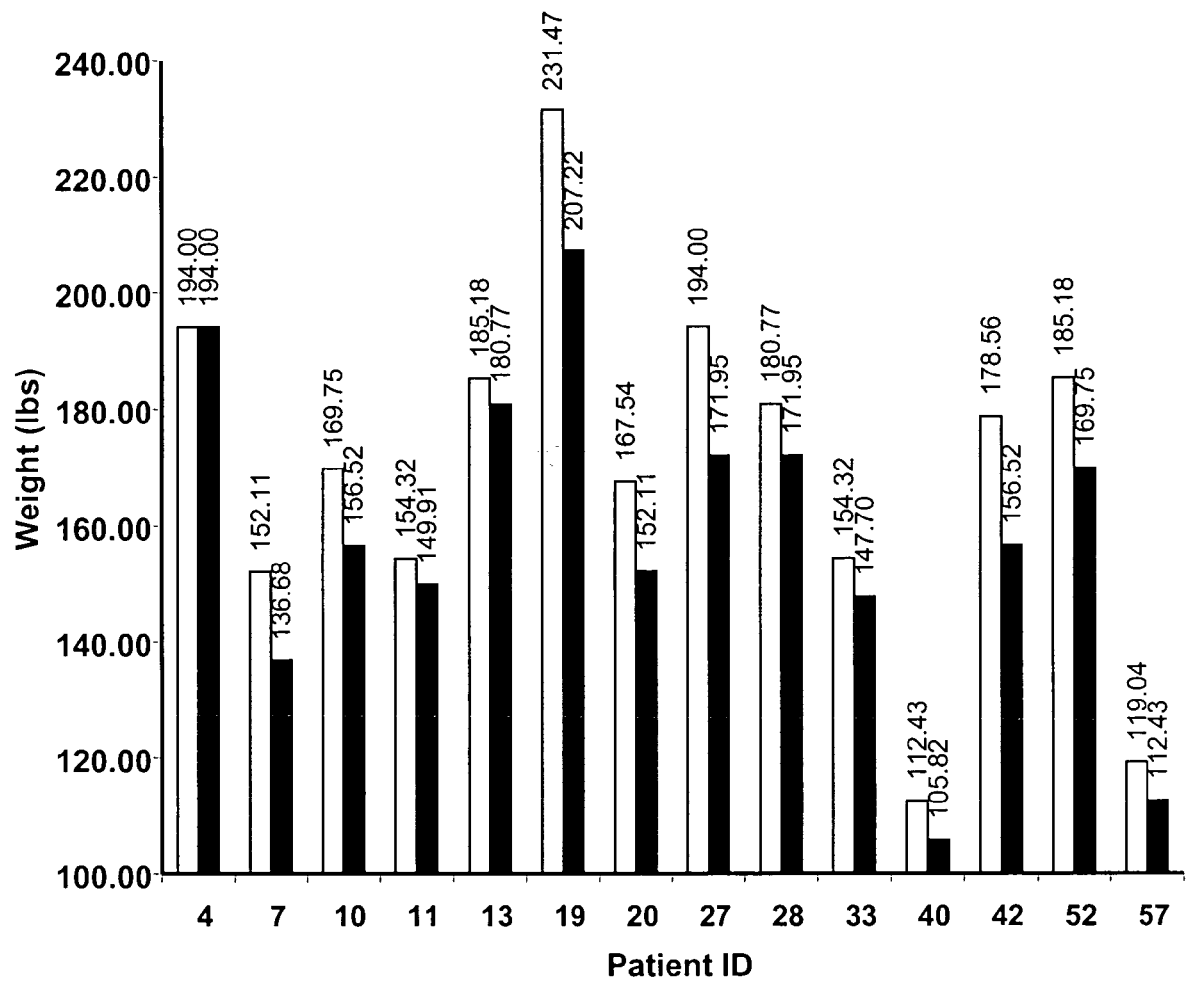

FIG. 9 illustrates shows the effect of the Free-B-Ring flavonoid and flavan extract on weight loss in 13 individuals orally administered 250 mg per day over a 90-day period. Individual weights (initial and final) are shown above each measurement for each human subject.

Figure 10:
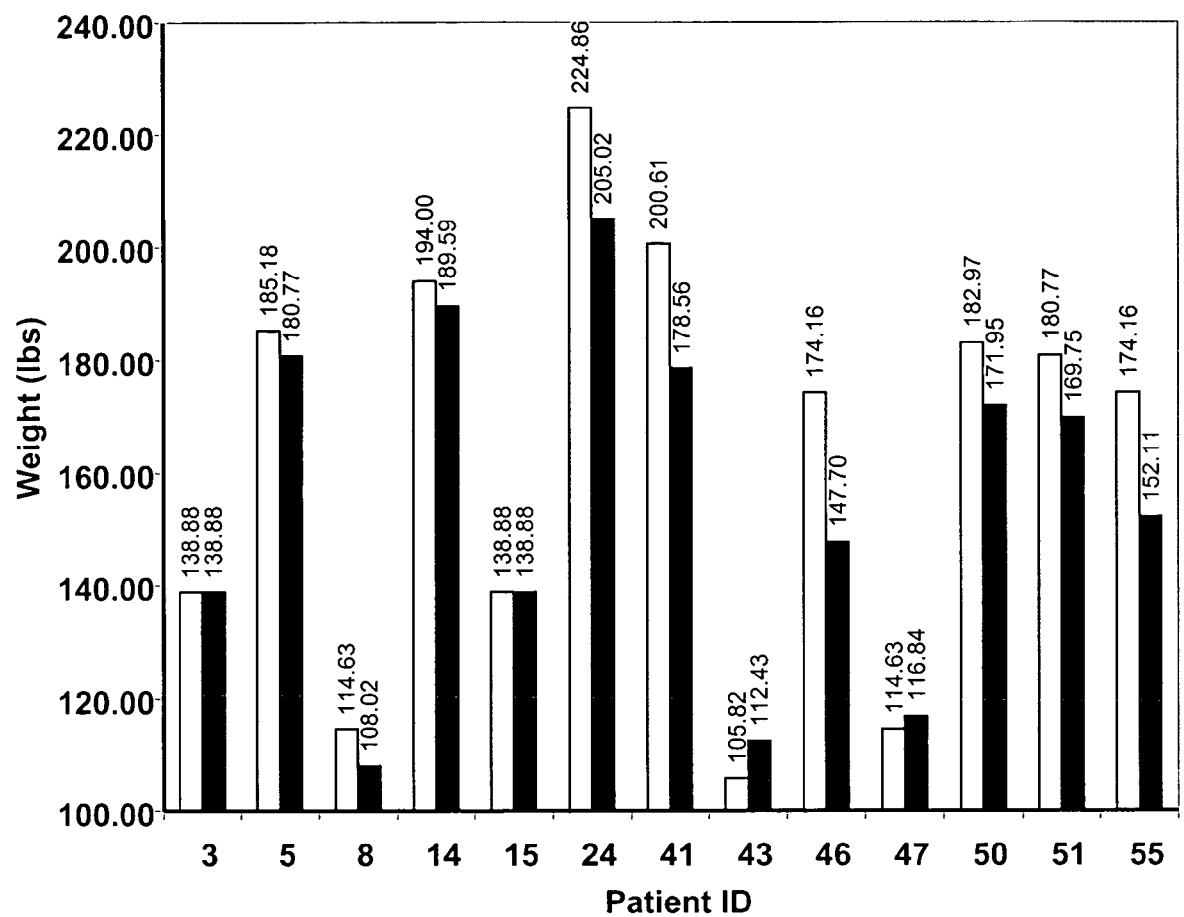

FIG. 10 illustrates the effect of the Free-B-Ring flavonoid and flavan extract on weight loss in 13 individuals orally administered 500 mg per day over a 90-day period. Individual weights (initial and final) are shown above each measurement for each human subject.

Figure 11:
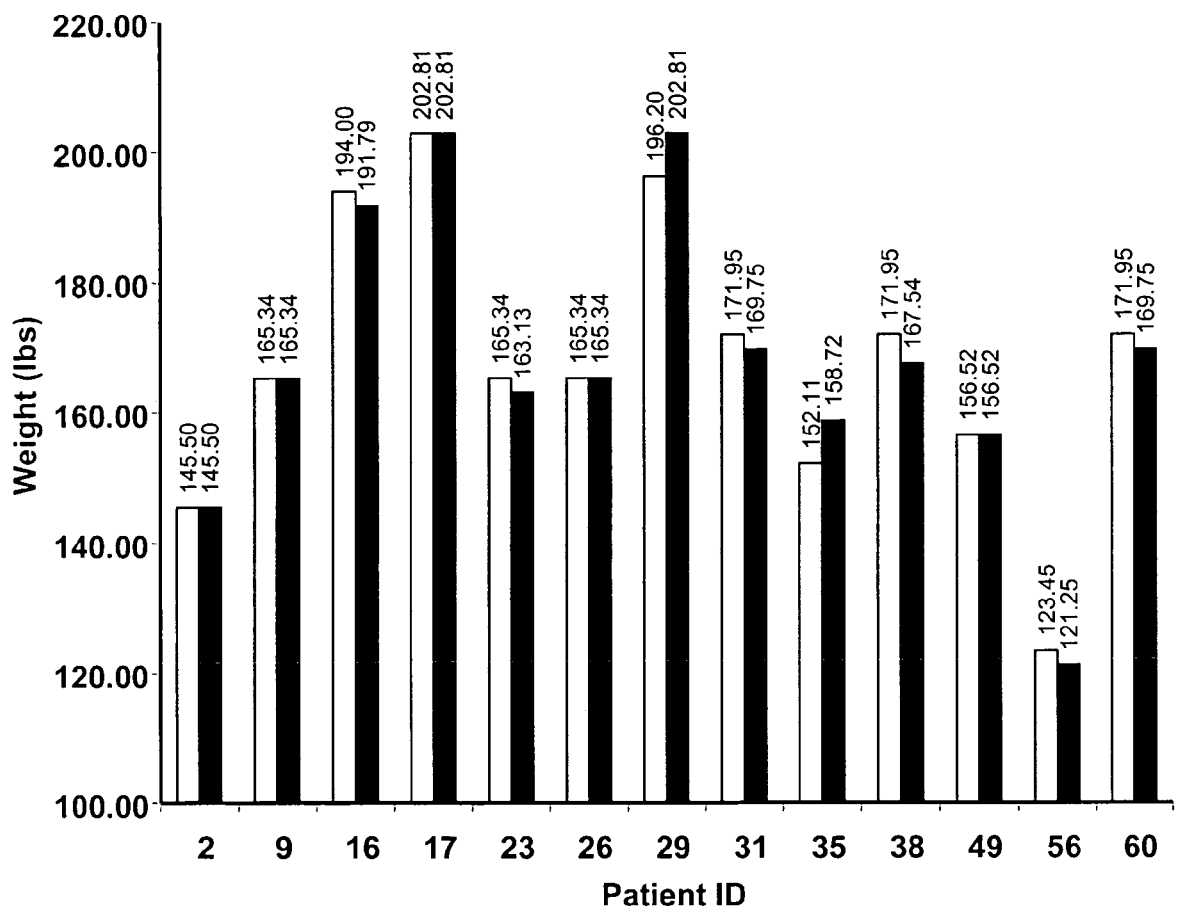

FIG. 11 depicts the effect on weight loss in 13 individuals orally administered a placebo over a 90-day period. Individual weights (initial and final) are shown above each measurement for each human subject.

Figure 12:
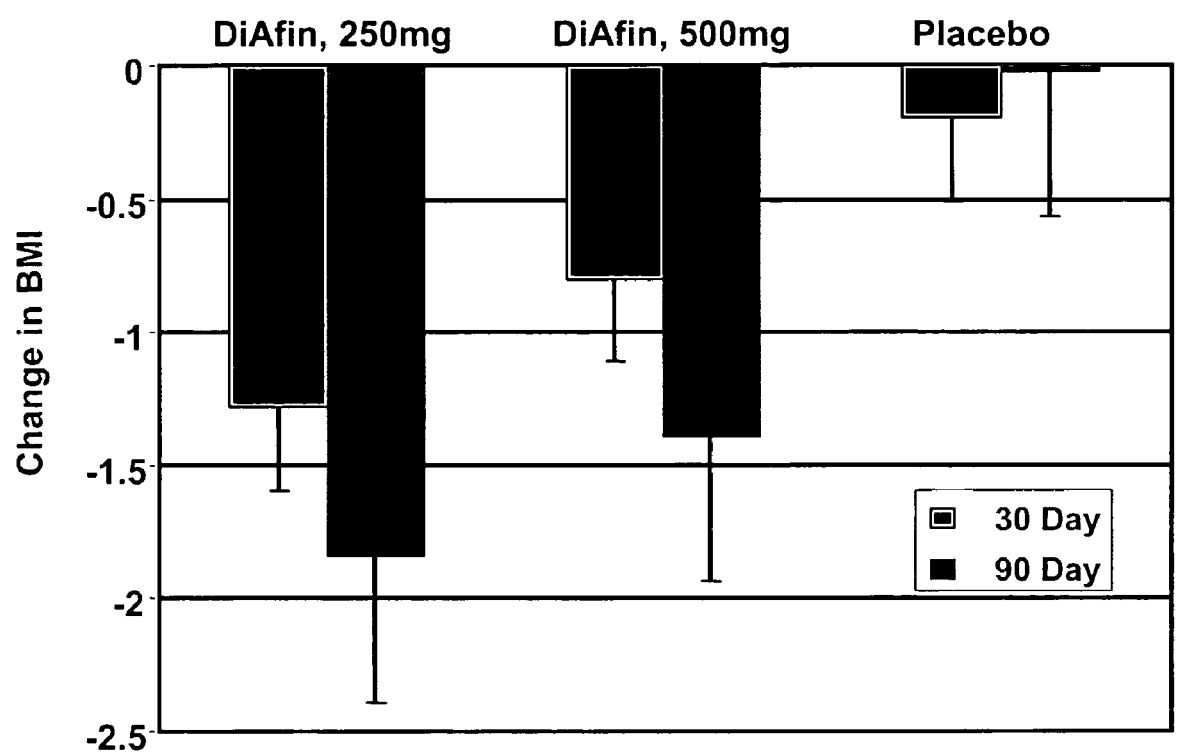

FIG. 12 illustrates the effect of the Free-B-Ring flavonoid and flavan extract on Body Mass Index (BMI) in individuals orally administered 250 and 500 mg per day versus placebo at 30 and 90 days. The SEM is also shown for each group.

Figure 13:
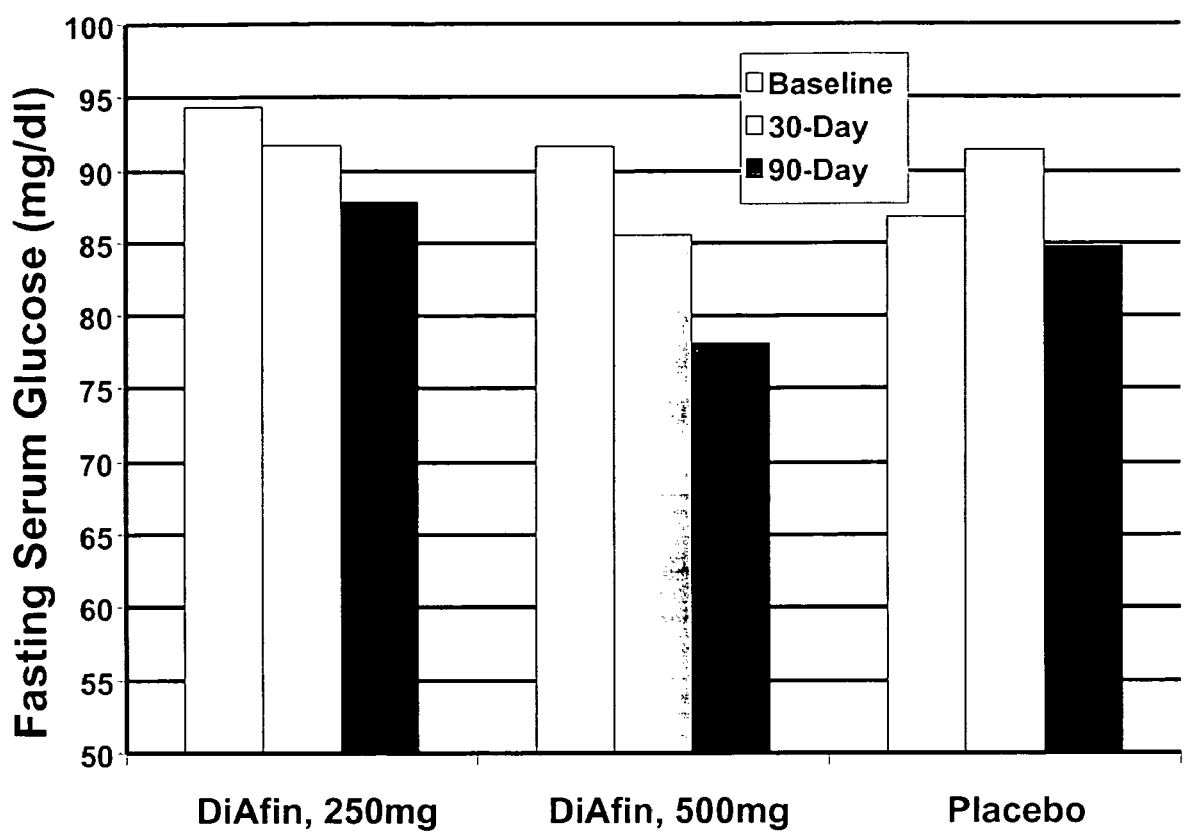

FIG. 13 illustrates the effect of the Free-B-Ring flavonoid and flavan extract on changes in blood glucose in individuals orally administered 250 and 500 mg per day versus placebo (baseline) at 0, 30 and 90 days.

Figure 14:
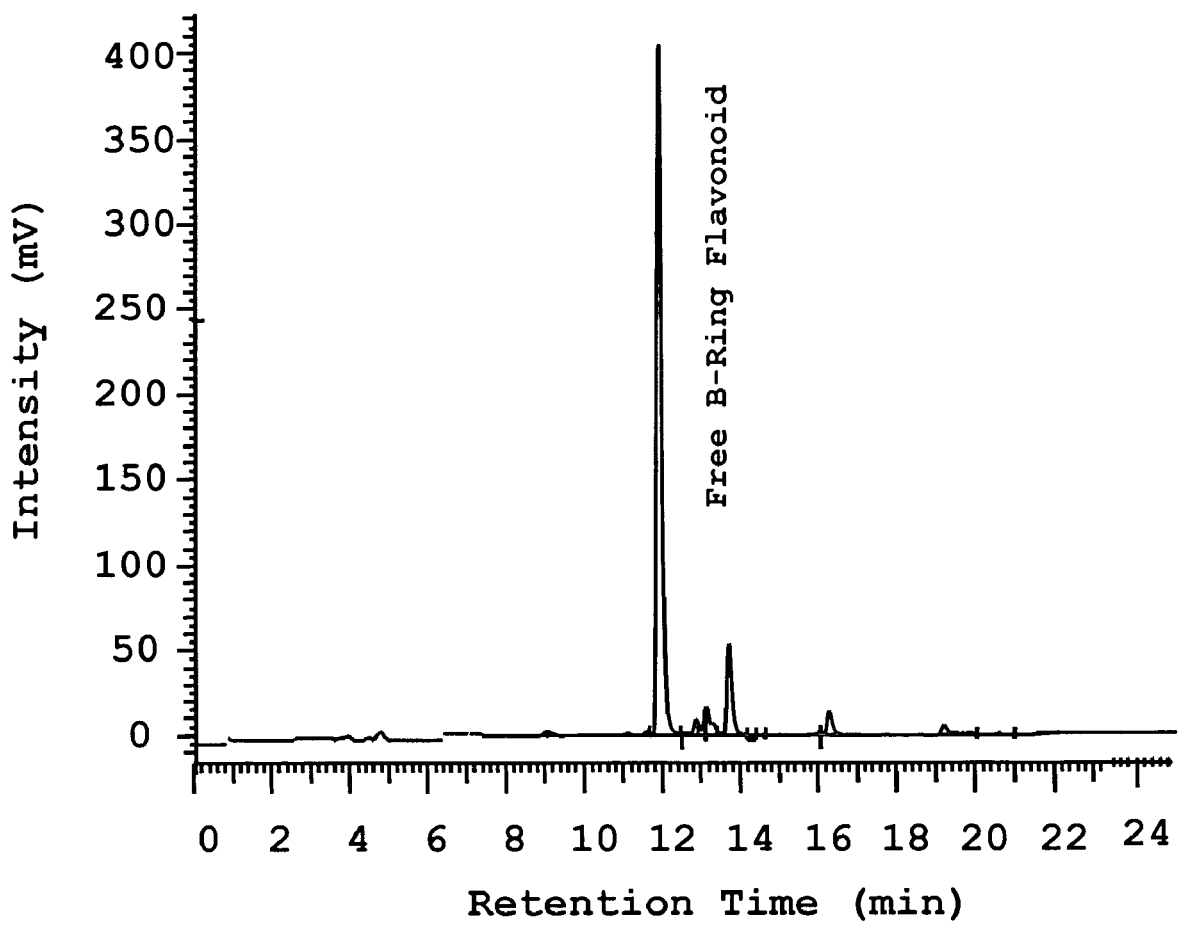
Figure 15:
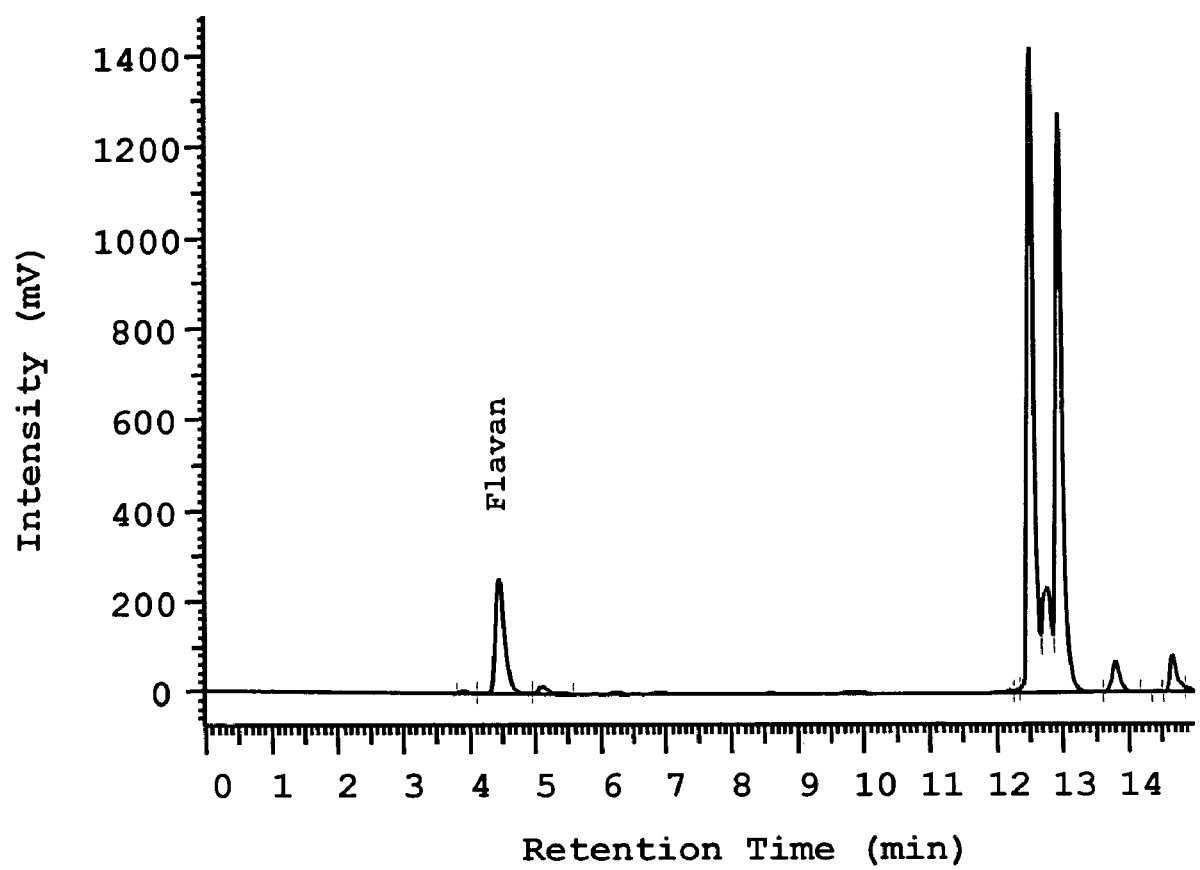

FIG. 14 illustrates the High Pressure Liquid Chromatography (HPLC) chromatogram of the mixture of Free-B-Ring flavonoids and flavans carried out under the conditions as described in Example 8. Using the described conditions the Free-B-Ring flavonoids eluted between 11 to 14 minutes and the flavans eluted between 3 to 5 minutes FIG. 15 depicts an HPLC chromatogram of the mixture of Free-B-Ring flavonoids and flavans carried out under the conditions as described in Example 9. Using the described conditions the two flavans (catechins and epicatechins) eluted between 4.5 to 5.5 minutes and the Free-B-Ring flavonoids (bacalein and bacalin) eluted between 12 and 13.5 minutes. Under the conditions described in Example 9, the separation is based upon differences in molar absorbtivity of the Free-B-Ring flavonoids and flavans.

DETAILED DESCRIPTION OF THE INVENTION

The present invention relates to a novel composition of matter comprised of a mixture of a blend of two specific classes of compounds—Free-B-Ring flavonoids and flavans—for use in the prevention and treatment of weight gain and obesity, as well as, other diseases and conditions resulting from high carbohydrate ingestion. The diseases and conditions include, but are not limited to, hyperlipidemia, high cholesterol, arteriosclerosis, atherosclerosis, syndrome X (metabolic syndrome), systemic inflammation conditions caused by obesity and diabetes, and hypertension.

Various terms are used herein to refer to aspects of the present invention. To aid in the clarification of the description of the components of this invention, the following definitions are provided.

It is to be noted that the term "a" or "an" entity refers to one or more of that entity; for example, a flavonoid refers to one or more flavonoids. As such, the terms "a" or "an", "one or more" and "at least one" are used interchangeably herein.

"Free-B-Ring Flavonoids" as used herein are a specific class of flavonoids, which have no substituent groups on the aromatic B ring, as illustrated by the following general structure:

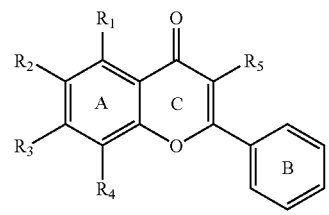

wherein $R_1, R_2, R_3, R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Flavans" as used herein refer to a specific class of flavonoids, which are generally represented by the following general structure:

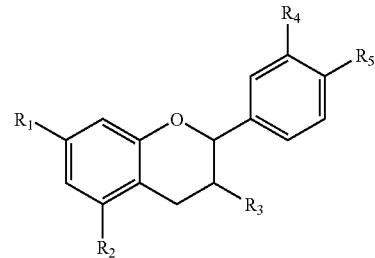

wherein $R_1, R_2, R_3, R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

Figure 1:
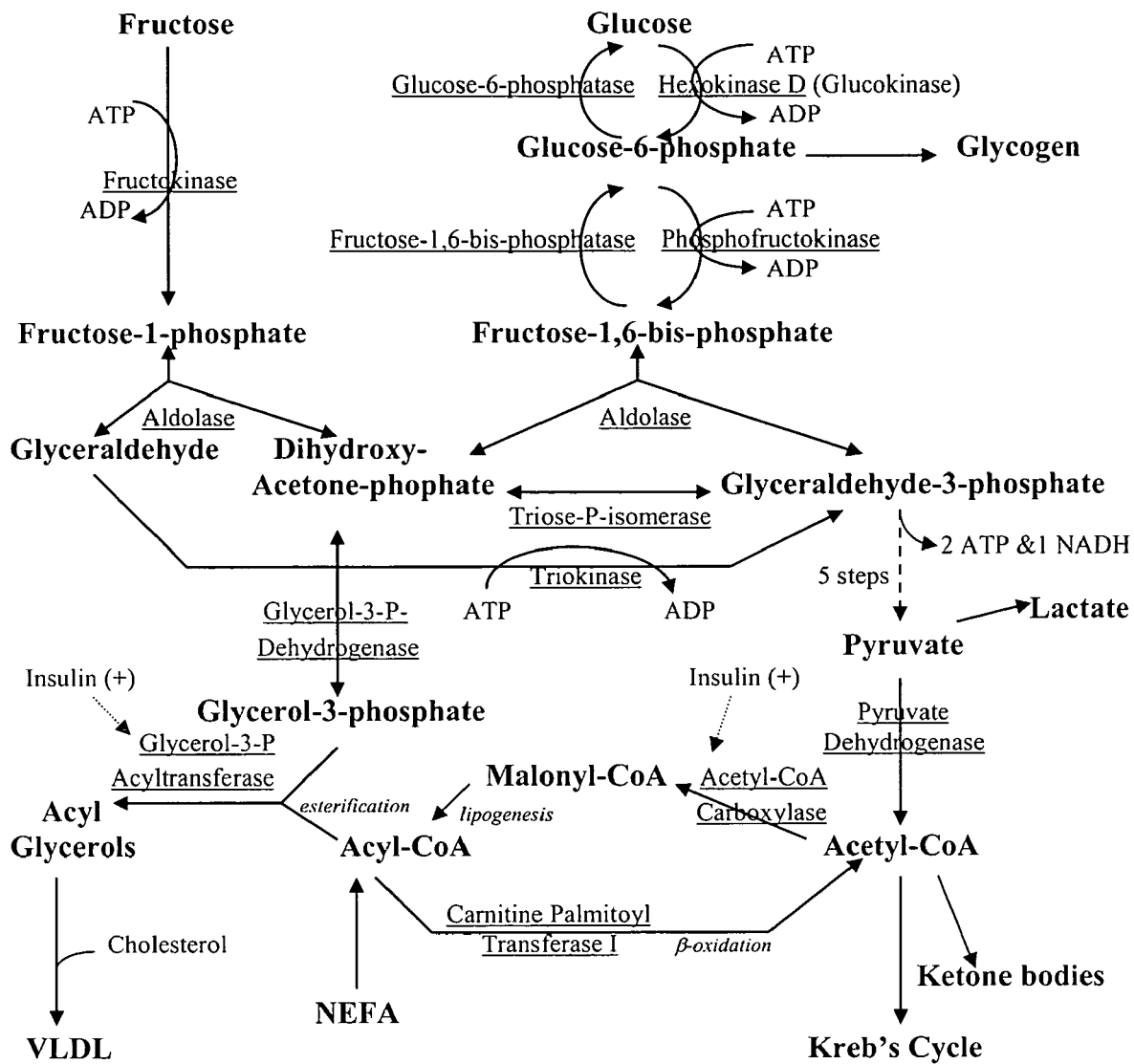
FIG. 1 depicts schematically the metabolism of fructose and glucose in the glycolytic and lipogenesis pathways in the liver.

"Fructose-induced lipogenesis" as used herein refers to the specific pathway of lipid formation from fructose that occurs through the production of the intermediate dihydroxy-acetone-phosphate followed by its conversion to glycerol-3-phosphate and subsequent esterification to acyl glycerols as illustrated schematically in FIG. 1.

"De novo lipogenesis" as used herein refers to the specific pathway of lipid formation from glucose that occurs through the production of the intermediate pyruvate, followed by its conversion to acetyl-CoA in a carboxylation reaction, which is converted to malonyl-CoA, which is then converted to acyl-CoA followed by esterification to acyl glycerols as illustrated schematically in FIG. 1.

"Sugar-induced lipogenesis" as used herein refers to both fructose-induced and de novo lipogenesis.

"Sugar" as used herein refers to both simple and complex carbohydrates including, but not limited to monosaccharides, disaccharides and polysaccharides. A monosaccharide is a simple sugar, including, but not limited to glucose, fructose and galactose. A disaccharide is a double sugar or a sugar that contains two molecules of a simple sugar, such as sucrose. Sugar as used herein also refers to the carbohydrates resulting from the break down or degradation of complex carbohydrates. A complex carbohydrate or polysaccharide is a carbohydrate that contains three or more molecules of a simple sugar. Complex carbohydrates include starch and glycogen. Sugars formed as a result of the degradation of complex carbohydrates include, but are not limited to, maltotriose, α-dextrin, maltose and other metabolically active disaccharides.

"Therapeutic" as used herein, includes treatment and/or prophylaxis. When used, therapeutic refers to humans, as well as, other animals.

"Pharmaceutically or therapeutically effective dose or amount" refers to a dosage level sufficient to induce a desired biological result. That result may be the alleviation of the signs, symptoms or causes of a disease or any other desired alteration of a biological system.

"Placebo" refers to the substitution of the pharmaceutically or therapeutically effective dose or amount sufficient to induce a desired biological that may alleviate the signs, symptoms or causes of a disease with a non-active substance.

A "host" is a living subject, human or animal, into which the compositions described herein are administered.

Note, that throughout this application various citations are provided. Each citation is specifically incorporated herein in its entirety by reference.

The present invention includes methods that are effective in inhibiting sugar induced weight gain and sugar induced obesity. The methods for inhibiting sugar induced weight gain and inhibiting sugar induced obesity are comprised of administering a composition comprising a mixture of Free-B-Ring flavonoids and flavans synthesized and/or isolated from a single plant or multiple plants to a host in need thereof.

The ratio of Free-B-Ring flavonoids to flavans can be in the range of 99.9:0.1 Free-B-Ring flavonoids:flavans to 0.1:99.9 Free-B-Ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of this invention the ratio of Free-B-Ring flavonoids:flavans in the composition of matter is 80:20. In a preferred embodiment the Free-B-Ring flavonoids are isolated from a plant or plants in the *Scutellaria* genus of plants and the flavans are isolated from a plant or plants in the *Acacia* genus of plants.

The present invention also includes a method for the prevention and treatment of sugar induced diseases and conditions. The method for preventing and treating sugar induced diseases and conditions is comprised of administering to a host in need thereof an effective amount of a composition comprising a mixture of Free-B-Ring flavonoids and flavans synthesized and/or isolated from a single plant or multiple plants and a pharmaceutically acceptable carrier. The ratio of Free-B-Ring flavonoids to flavans can be in the range of 99.9:0.1 Free-B-Ring flavonoids:flavans to 0.1:99.9 Free-B-Ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of this invention the ratio of Free-B-Ring flavonoids:flavans in the composition of matter is 80:20. In a preferred embodiment the Free-B-Ring flavonoids are isolated from a plant or plants in the *Scutellaria* genus of plants and the flavans are isolated from a plant or plants in the *Acacia* genus of plants.

The present invention further includes methods for genomic reduction NFκB and subsequent decrease in TNFα and IL-6 levels, which are prime markers for obesity and other inflammatory diseases. The method for genomic reduction of NFκB and subsequent decrease in TNFα and IL-6 levels is comprised of administering to a host in need thereof an effective amount of a composition comprising a mixture of Free-B-Ring flavonoids and flavans synthesized and/or isolated from a single plant or multiple plants. The ratio of Free-B-Ring flavonoids to flavans can be in the range of 99.9:0.1 Free-B-Ring flavonoids:flavans to 0.1:99.9 Free-B-Ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of this invention the ratio of Free-B-Ring flavonoids:flavans in the composition of matter is 80:20. In a preferred embodiment the Free-B-Ring flavonoids are isolated from a plant or plants in the *Scutellaria* genus of plants and the flavans are isolated from a plant or plants in the *Acacia* genus of plants.

The Free-B-Ring flavonoids that can be used in accordance with the following include compounds illustrated by the general structure set forth above. The Free-B-Ring flavonoids of this invention may be obtained by synthetic methods or may be isolated from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae, and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Orig-*

*anum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus*, and *Alpinia*.

The flavonoids can be found in different parts of plants, including but not limited to stems, stem barks, twigs, tubers, roots, root barks, young shoots, seeds, rhizomes, flowers and other reproductive organs, leaves and other aerial parts. Methods for the isolation and purification of Free-B-Ring flavonoids are described in U.S. application Ser. No. 10/091,362, filed Mar. 1, 2002, entitled "Identification of Free-B-Ring Flavonoids as Potent COX-2 Inhibitors," which is incorporated herein by reference in its entirety.

The flavans that can be used in accordance with the method of this invention include compounds illustrated by the general structure set forth above. The flavans of this invention are isolated from a plant or plants selected from the *Acacia* genus of plants. In a preferred embodiment, the plant is selected from the group consisting of *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium*.

The flavans can be found in different parts of plants, including but not limited to stems, stem barks, trunks, trunk barks, twigs, tubers, roots, root barks, young shoots, seeds, rhizomes, flowers and other reproductive organs, leaves and other aerial parts. Methods for the isolation and purification of flavans are described in U.S. application Ser. No. 10/104,477, filed Mar. 22, 2002, entitled "Isolation of a Dual Cox-2 and 5-Lipoxygenase Inhibitor from *Acacia*," which is incorporated herein by reference in its entirety.

The method of this invention can be used to treat and prevent a number of obesity associated diseases and conditions including, but not limited to, hyperlipidemia, high cholesterol, arteriosclerosis, atherosclerosis, syndrome X (metabolic syndrome), systemic inflammation conditions caused by obesity and diabetes, and hypertension.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a host in need thereof a therapeutically effective amount of a mixture of Free-B-Ring flavonoids and flavans synthesized and/or isolated from a single plant or multiple plants. In a preferred embodiment the composition is administered in a dosage selected from 0.01 to 200 mg/kg of body weight.

The present invention implements a strategy that combines a series of in vivo weight measurement studies as well as in vitro biochemical, cellular, and gene expression screens to identify active plant extracts that specifically inhibit fructose metabolism as it pertains to increase in lipid and fat content in the body, enzymatic activity of metabolic enzymes, impact on mRNA gene expression and lipogenesis in general. Free B-ring flavonoids and flavans were tested for their ability to inhibit fructose-induced obesity when administered by oral gavage.

Figure 2:
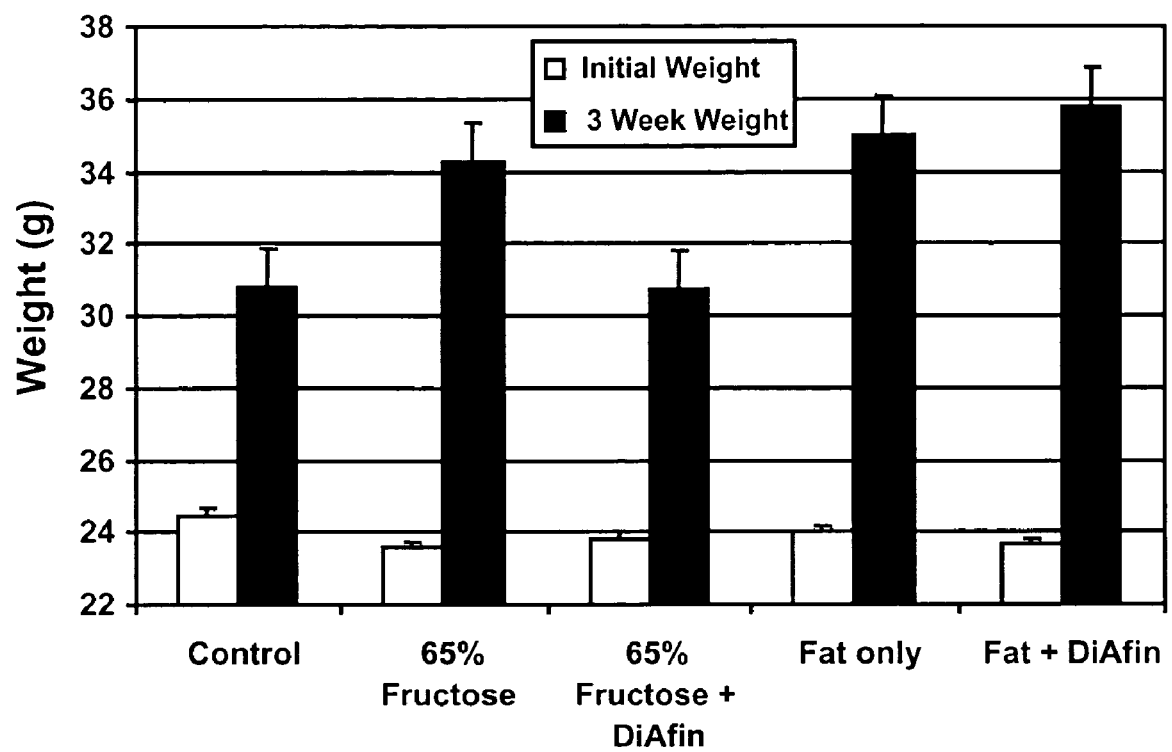
FIG. 2 depicts graphically the effect of a mixture of Free-B-Ring flavonoids and flavans administered daily for 3 weeks, on fructose induced weight gain and fat-induced weight gain in ICR female mice fed a normal diet, a diet supplemented with 65% fructose or a diet supplemented with fat, as described in Example 1. Mice maintained on a normal diet served as a control. Two test groups were given either 65% fructose only or fat only. This figure demonstrates that a mixture of Free-B-Ring flavonoids and flavans prevents excess weight gain resulting from the consumption of fructose.

Example 1 describes an experiment designed to determine the effect of a mixture of Free-B-Ring flavonoids and flavans on weight gain resulting from a diet supplemented with fructose or fat for three weeks. The results are set forth in FIG. 2. With reference to FIG. 2, it can be seen that animals that were given fat, together with the extract gained approximately the same amount of weight as those given fat only and no extract. However, mice given fructose, together with extract gained the same amount of weight as the control group, which were fed a normal diet. This result illustrates that a composition of matter comprised of a mixture of Free-B-Ring flavonoids (60-90% based on HPLC) and flavans (10-60% based on HPLC) was effective in preventing excess weight gain resulting from the consumption of fructose. While not limited by theory, it is presumed that this result is due to a change in fructose utilization in the lipogenesis pathway.

Figure 3:
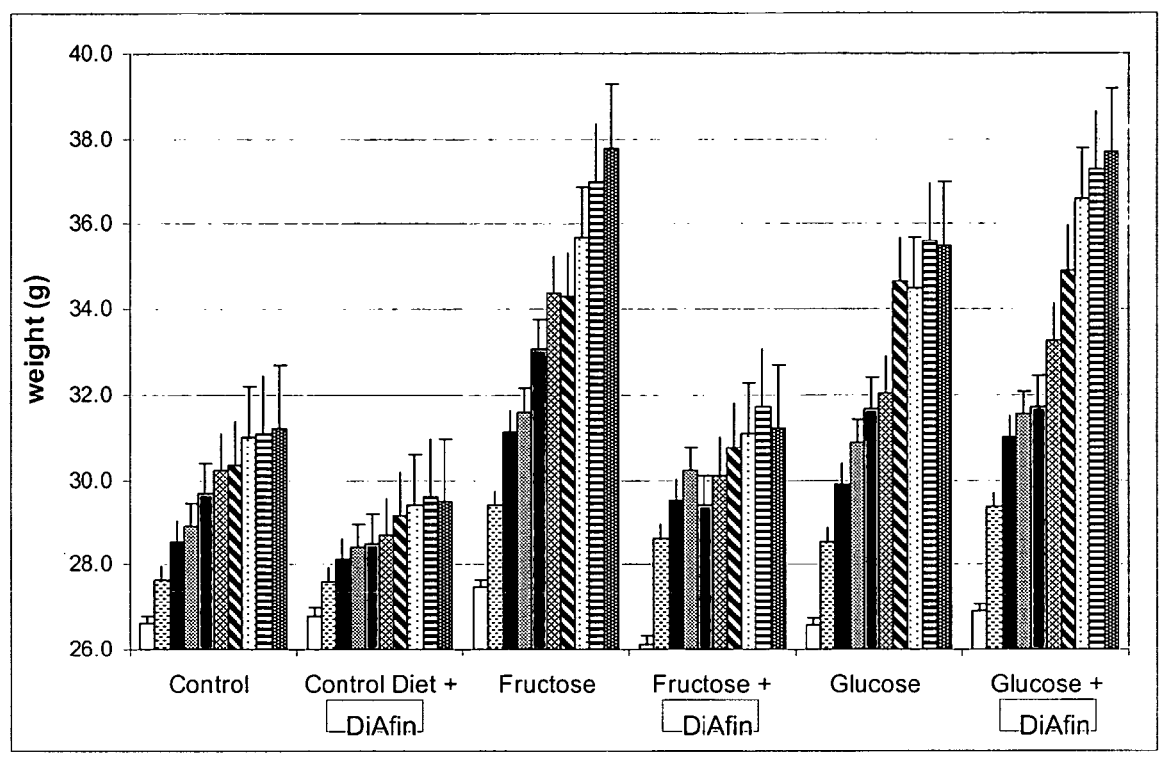
FIG. 3 illustrates graphically the effect of a mixture of Free-B-Ring flavonoids and flavans administered daily on fructose versus glucose induced weight gain in ICR mice fed a normal diet (control), a diet supplemented with 65% fructose for 8 weeks and a diet supplemented with 65% glucose for 8 weeks as described in Example 3. Weights were measured weekly and the mean plotted for each group. The Standard Error of the Mean (SEM) is shown for each group at each week.

Example 2 describes an experiment designed to illustrate the effect of a mixture of Free-B-Ring flavonoids and flavans on weight gain resulting from a diet supplemented with fructose and glucose for eight weeks. The results are set forth in FIG. 3. With reference to FIG. 3 it can be seen that animals that were given glucose, together with extract gained approximately the same amount of weight as those given glucose only and no extract. However, the mice given fructose together with extract gained significantly less weight than the mice given fructose only and no extract. Mice given sucrose or commercial sources of fructose syrup showed intermediate weight gain under the conditions of this experiment (data not shown).

Figure 4:
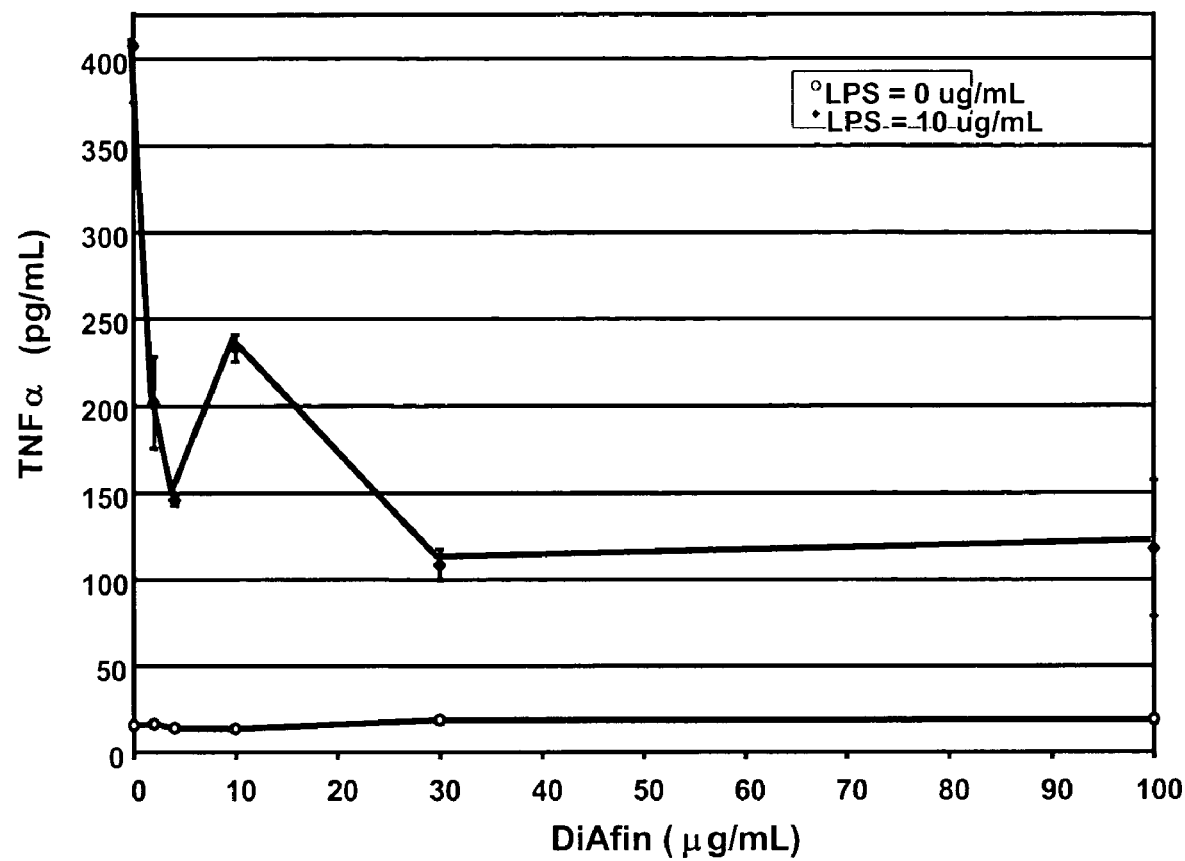
FIG. 4 depicts the effect of a mixture of Free-B-Ring flavonoids and flavans (80:20) on the lipopolysaccharide (LPS)- induced level of TNFα in peripheal blood monocytes (PBMC) following exposure to the lipopolysaccharide in conjunction with different concentrations of the Free-B-Ring flavonoid and flavan mixture for one hour. The level of TNFα is expressed in pg/mL. The standard deviation is shown for each data point.

Example 3 illustrates the effect of a mixture of Free-B-Ring flavonoids and flavans on the secreted concentration of TNFα. The results are set forth in FIG. 4. With reference to FIG. 4, it can be seen that the extract decreased TNFα secreted into the cell culture supernatant substantially over a wide range of concentrations from 2 to 100 µg/mL. Since TNFα is a marker in obesity, the extract has a significant impact by decreasing this pro-inflammatory cytokine in primed inflammatory cells.

Example 4 illustrates the effect of a mixture of Free-B-Ring flavonoids and flavans on the secreted concentration of IL-6. The results are set forth in FIG. 5. With reference to FIG. 5, it can be seen that the extract decreased IL-6 secreted into the cell culture supernatant substantially over a wide range of concentrations from 2 to 100 µg/mL. Since IL-6 is a marker in obesity, the extract has a significant impact by decreasing this pro-inflammatory cytokine in primed inflammatory cells.

The drop in TNFα as well as IL-6 could be caused by disruption of the transcription factor NFκB, since both gene promoters are activated by NFκB. To test this hypothesis, the effect of a mixture of Free-B-Ring flavonoids and flavans on the gene expression transcription factor NFκB was evaluated as described in Example 5. The results are set forth in FIG. 6, which illustrates graphically relative NFκB gene expression as a function of the concentration of extract. As can be seen in FIG. 6, NFκB showed a 2.7-fold down-regulation of expression at the highest concentration of extract. Small changes in NFκB have been shown to down-regulate gene expression of other genes to a high extent.

The effect of a mixture of Free-B-Ring flavonoids and flavans on gene expression of TNFα is illustrated in FIG. 7. As can be seen, the relative gene expression for TNFα was down-regulated almost 10-fold under the conditions described in Example 5. This result together with the reduction of cytokines found in protein assays suggests that NFκB may be inhibited by Free-B-Ring flavonoid/flavan extract.

There are two key enzymes in the fructose and glucose metabolic pathways, aldolase A and aldolase B, which may be effected by the action of the Free-B-Ring flavonoid/flavan extract. With reference to FIG. 1, aldolase B catalyzes the conversion of fructose-1-phophate to glyceraldehyde and dihydroxyacetone phosphate and aldolase A catalyzes the conversion of fructose-1,6-bis-phosphate to glyceraldehyde-3-phosphate and dihydroxyacetone phosphate, respectively. Trioseisomerase catalyzes the conversion of dihydroxyacetone phosphate to glyceraldehyde-3-phosphate, while triokinase with the expenditure of a single ATP molecule catalyzes the conversion of glyceraldehyde to glyceraldehyde-3-phosphate, thus linking the fructose catalytic and glycolytic pathways. Aldolase B is not commercially available, therefore aldolase A which can also catalyze the conversion of fructose-1,6-bis-phosphate to glyceraldehyde-3-phosphate and dihydroxyacetone phosphate, was employed to determine the potential effect of the extract on these enzymes in vitro, as described in Example 6. The results are set forth in FIG. 8, which illustrates graphically the absorbance of the reaction mixture versus time at various inhibitor concentrations. This figure illustrates that there is a decrease in the formation of product as the concentration of extract is increased. This observation suggests the direct inhibition of aldolase in the conversion of fructose-1-phosphate to glyceraldehyde and dihydroxyacetone phosphate by the extract. Thus, while not limited by theory, the inhibition of aldolase in the fructose catalytic pathway may contribute to the mechanism that causes lower weight gain in mice whose diet has been supplemented with fructose and extract.

Example 7 describes a human clinical trial initiated to test the effectiveness of the extract on human weight loss. The results are set forth in FIGS. 9-13. FIG. 9 depicts the effect of the Free-B-Ring flavonoid and flavan extract on weight loss in 13 individuals orally administered 250 mg per day over a 90-day period. Individual weights (initial and final) are shown above each measurement for each subject. With reference to FIG. 9, it can be seen that at dosage of 250 mg per day a significant weight loss was observed in 13 of 14 individuals remaining in the study after 90 days. Only one subject (subject 4) did not show weight loss. The weight data differences between day 0 and day 90 showed a statistical significance with $p<0.001$.

FIG. 10 illustrates the effect of the Free-B-Ring flavonoid and flavan extract on weight loss in 13 individuals orally administered 500 mg per day over a 90-day period. Individual weights (initial and final) are shown above each measurement for each subject. As can be seen in FIG. 10, when the dosage was increased to 500 mg per day, the weight loss showed a different pattern. Subjects with higher BMIs tended to lose more weight than those with lower BMIs. A stratification occurred in which lower weight subjects either did not lose weight or even gained in some cases (see subjects 3, 15, 43, and 47). Thirteen subjects completed the study. The statistical significance for this data showed a $p <0.011$.

FIG. 11 depicts the effect on weight loss in 13 individuals orally administered a placebo over a 90-day period. Individual weights (initial and final) are shown above each measurement for each human subject. As can be seen in this figure, the placebo group showed very little change in weight for the 13 subjects that completed the trial.

FIG. 12 illustrates the effect of the Free-B-Ring flavonoid and flavan extract on BMI in individuals orally administered 250 and 500 mg per day versus placebo at 30 and 90 days. As can be seen in FIG. 12, when the average BMI for all three groups was plotted, significant differences are observed. At a dose of 250 mg per day versus the placebo, the $p<0.075$, while the 500 mg per day dose showed a $p<0.005$. Within group analysis showed $p<0.004$ for 250 mg dose versus $p<0.051$ for the 500 mg per day dose.

FIG. 13 illustrates the effect of the Free-B-Ring flavonoid and flavan extract on changes in blood glucose in individuals orally administered 250 and 500 mg per day versus placebo at 0, 30 and 90 days. Thus, in addition to the decrease in weight and beneficial change in BMI, blood glucose levels went down in the 250 and 500 mg per day groups with the latter showing the greatest change. The blood glucose levels of those receiving placebo however, were relatively unchanged over the testing period. The fasting serum glucose data showed significance compared to the baseline data with a $p<0.018$ for the 500 mg per day dose and $p<0.014$ for the 250 mg per day dose. The fasting serum glucose data showed significance compared to the baseline data with a $p<0.018$ for the 500 mg per day dose and $p<0.014$ for the 250 mg per day dose.

Determination of purity and quantification of the Free B-ring flavonoid and flavan mixture was accomplished by HPLC analysis using two different methods as described by Examples 8 and 9. The results are set forth in FIGS. 14 and 15. With reference to FIG. 14, the Free B-ring flavonoids (primarily baicalein and baicalin) were measured after HPLC analysis to be >60% of the total eluted area. Because flavans have lower overall absorbtivity, using the method described in Example 9, approximately three times as much extract was loaded on the HPLC column and eluted under isocratic conditions. With reference to FIG. 15, the flavans (catechin and epicatechin) were measured after HPLC analysis to be >10% of the total eluted area.

Individual standardized extract containing high concentrations of Free-B-Ring flavonoids (60-90% based on HPLC) and flavans (10-60% based on HPLC), as well as, the combined extract containing a mixture of Free-B-Ring flavonoids and flavans were tested for toxicity in mice with both chronic and acute administration. In the chronic administration protocol, mice were fed the test articles by oral gavage with daily doses of 90 mg/kg (equivalent to the human daily dose of 500 mg), 450 mg/kg (five times the daily dose equivalent) and 900 mg/kg (ten times the daily dose equivalent). The treated mice showed no adverse effects in terms of weight gain, physical appearance and behavior. Gross necropsy results showed no organ abnormalities and histology of both the stomach and liver showed no differences compared to untreated control mice. Full blood work measuring electrolytes, blood proteins, blood enzymes, and liver enzymes showed no abnormalities compared to the untreated control mice.

In the acute administration protocol, individual standardized extract containing high concentrations of Free-B-Ring flavonoids (60-90% based on HPLC) and flavans (10-60% based on HPLC), as well as, the combined extract containing a mixture of both Free-B-Ring flavonoids and flavans were administered at 2 grams/kg (20 times the daily dose equivalent). Treated mice showed no abnormalities in weight gain, appearance, behavior, gross necropsy appearance of organs, histology of stomach and liver or blood work.

Based on the ability of Free-B-Ring flavonoids and flavans to directly inhibit sugar-induced obesity, as well as, their activity in genomically reducing NFκB the key transcription factor in the regulation of the pro-inflammatory cytokine markers for obesity, TNFα and IL-6, the composition described herein will effectively inhibit weight gain, sugar-based lipogenesis and systemic inflammation. Additionally, the ability of Free-B-Ring flavonoids and flavans to directly inhibit aldolase, which converts fructose-1-phosphate to glyceraldehydes and dihydroxyacetone phosphate, will result in a decrease in the amount of substrate available for synthesis of fat in both de novo and fructose-induced lipogenesis.

The following examples are provided for illustrative purposes only and are not intended to limit the scope of the invention.

EXAMPLES

Example 1

Effect of a Mixture of Free-B-Ring Flavonoids and Flavans on Weight Gain Resulting from a Diet Supplemented with Fructose or Fat for Three Weeks To investigate the effect that a composition of matter comprised of a mixture of Free B-Ring flavonoids and flavans has weight gain, a defined plant extract containing Free-B-Ring flavonoids isolated from *Scutellaria baicalensis* and flavans isolated from *Acacia catechu* in a ratio of 80:20 (Free-B-Ring flavonoids:flavans) was used. This composition of matter was formulated as described in U.S. application Ser. No. 10/427, 746, filed Apr. 30, 2003, entitled "Formulation With Dual Cox-2 And 5-Lipoxygenase Inhibitory Activity," which is incorporated herein by reference in its entirety.

Six-week-old ICR female mice (ten per test group) (Harlan Laboratories) were gavaged with the extract in water at a therapeutic dose of 100 mg/kg. One group of mice were fed their normal diet and given a 65% solution of fructose as their drinking water, administered ad libitum. A second group of mice were fed a diet that was supplemented with fat and administered ad libitum. Two test groups were given either 65% fructose in their water (without extract) or their diet was supplemented with fat ad libitum (without extract). The results are set forth in FIG. 2.

Example 2

Effect of a Mixture of Free-B-Ring Flavonoids and Flavans on Weight Gain Resulting from a Diet Supplemented with Fructose and Glucose for Eight Weeks This study was performed generally in the same manner as described in Example 1, using six-week old ICR female mice (ten per test group) (Harlan Laboratories) as the test subjects and an 80:20 mixture of Free-B-Ring flavonoids:flavans formulated as described in as described in U.S. application Ser. No. 10/427,746, filed Apr. 30, 2003, entitled "Formulation With Dual Cox-2 And 5-Lipoxygenase Inhibitory Activity," which is incorporated herein by reference in its entirety. The results are set forth in FIG. 3.

With reference to FIG. 3 the "control" group was fed a balanced diet as recommended by the vendor. A second "control" group was also given the extract at 100 mg/kg by gavage. Two test groups received the control diet plus 65% fructose ad libitum in their water. One of these groups was gavaged daily with 100 mg/kg of extract. The final two test groups received the control diet plus 65% glucose ad libitum in their water. One of these groups was gavaged daily with 100 mg/kg of extract. After eight weeks, the average weights were plotted with the standard error of the mean (SEM) shown on the graph.

Example 3

Effect of a Mixture of Free-B-Ring Flavonoids and Flavans on the Concentration of TNFα

Peripheral blood monocytes (PBMCs) from human blood donors were isolated using a Histopaque gradient (Sigma). The cells were then cultured in RPMI 1640 supplemented with 1% bovine serum albumin for approximately 12 hours before being treated with lipopolysaccharide (LPS) at 10 mg/mL to induce inflammation in a one hour incubation in the presence of various concentrations of the 80:20, Free-B-Ring flavonoid:flavan extract. The results are set forth in FIG. 4.

Example 4

Effect of a Mixture of Free-B-Ring Flavonoids and Flavans on the Concentration of IL-6

Peripheral blood monocytes (PBMCs) from human blood donors were isolated using a Histopaque gradient (Sigma). The cells were then cultured in RPMI 1640 supplemented with 1% bovine serum albumin for approximately 12 hours before being treated with lipopolysaccharide (LPS) at 10 µg/mL to induce inflammation in a six hour incubation in the presence of various concentrations of the 80:20, free B-ring flavonoid:flavan extract. The results are set forth in FIG. 5. The extract decreased IL-6 secreted into the cell culture supernatant substantially over a wide range of concentrations from 2 to 100 µg/mL. Since IL-6 is a marker in obesity, the extract has significant impact by decreasing this pro-inflammatory cytokine in primed inflammatory cells.

Example 5

Effect of a Mixture of Free-B-Ring Flavonoids and Flavans on the Gene Expression of the Transcription Factor NFκB and on the Gene Expression of TNFα

PBMCs were induced with 1 mg/ml LPS for 18 hours and co-cultured with increasing amounts of the Free-B-Ring flavonoid:flavan extract. RNA was then isolated (Qiagen), reverse transcribed to DNA, and subjected to PCR using the TaqMan system and pre-validated primers for both NFκB and TNFα in quantitative PCR (ABI). Relative gene expression was measured in the presence of 0 to 100 µg/mL of extract. The results are set forth in FIGS. 6 and 7.

Example 6

Effect of a Mixture of Free-B-Ring Flavonoids and Flavans on the Enzyme Adolase A Aldolase A (Sigma) at 1 unit/µL was added to a solution of 4 mM fructose-1-phosphate in a buffer containing 100 µM EDTA and 3.5 mM hydrazine sulfate, pH 7.5 (Jagannathan et al. (1956) Biochem. J. 63:94-105) and the extract ranging in concentration from 0 to 65 µg/mL at 25° C. The reaction was initiated by the addition of the enzyme and monitored for 10 minutes at 240 nm. The results are set forth in FIG. 8, which illustrates graphically the absorbance of the reaction mixture versus time at various inhibitor concentrations.

Example 7.

Effect of the Free-B-Ring Flavonoid and Flavan Extract on Human Weight Loss

A 90-day, IRB reviewed, double-blind, placebo control trial was initiated with 15 subjects per group in three different groups: 1) Placebo; 2) 250 mg per day (dosed at 125 mg b.i.d.); and 3) 500 mg per day (dosed at 250 mg b.i.d.). The subjects were age and sex matched. Subjects were given the placebo or extract orally in a concealed pill form and their weights, BMI and blood glucose levels were monitored at 0, 30, 60 and 90 days. No advice was given to the patients on whether they were receiving a weight loss product or whether they should modify their eating or exercising habits. The results are set forth in FIGS. 9-13.

Example 8

Quantification of the Mixture of Free-B-Ring Flavonoids and Flavans by Reverse Phase High Pressure Liquid Chromatography (HPLC) (Method 1)

The mixture of Free-B-Ring flavonoids and flavans (20 mL of a 1.13 mg/mL standardized extract) in 80%:20% methanol:tetrahydrofuran was loaded onto a Phenomenex Luna C-18 column (250×4.6 mm, 5 mm bead size) and eluted with a 1.0 mL/min, linear 80% A to 20% A gradient for 19 minutes (A=0.1% (v/v) phosphoric acid; B=acetonitrile) at 35° C. As can be seen in FIG. 14, under these conditions the Free-B-Ring flavonoids (bacalein and bacalin) eluted as the major peak between 11 to 14 minutes and the flavans (catechins and epicatechins) eluted as the minor peak at approximately 3 to 5 minutes. The amount of Free-B-Ring flavonoids and flavans were determined by measuring the area under each curve and comparison with known standards.

Example 9

Quantification of the Mixture of Free-B-Ring Flavonoids and Flavans by Reverse Phase Isocratic HPLC (Method 2)

The mixture of Free-B-Ring flavonoids and flavans (20 mL of a 3.55 mg/mL standardized extract) in 80%:20% methanol: water was loaded onto a Phenomenex Luna C-18 column (250×4.6 mm, 5 mm bead size) and eluted isocratically with 80% A (A=0.1% (v/v) phosphoric acid; B=acetonitrile) at 35° C. As can be seen in FIG. 15, under these conditions the two flavans (catechins and epicatechins) eluted between 4.5 to 5.5 minutes and the Free-B-Ring flavonoids (bacalein and bacalin) eluted between 12 and 13.5 minutes in the washout. Quantification of the flavan peaks was performed as described in Example 8.

What is claimed is:

1. A method for inhibiting fructose-induced weight gain comprising administering to a host in need thereof an effective amount of a composition comprised of a mixture of an extract of a plant containing Free-B-Ring flavonoids and an extract of a plant containing flavans, wherein the active ingredients in said mixture comprise at least baicalin and catechin and wherein said mixture contains no ephedra, ephedrine, pseudoephedrine or ephedrine like substance.

2. The method of claim 1 wherein the ratio of Free-B-Ring flavonoid to flavan in said composition is selected from the range of 99.9:0.1 Free-B-Ring flavonoid:flavan to 0.1:99.9 of Free-B-Ring flavonoid:flavan.

3. The method of claim 2 wherein the ratio of Free-B-Ring flavonoid:flavan in the composition of matter is about 80:20.

4. The method of claim 1 wherein said Free-B-Ring flavonoid and said flavan are isolated from a plant part selected from the group consisting of stems, stem barks, trunks, trunk barks, twigs, tubers, roots, root barks, young shoots, seeds, rhizomes, flowers and other reproductive organs, leaves and other aerial parts.

5. The method of claim 1 wherein said Free-B-Ring flavonoid is isolated from a plant family selected from the group consisting of Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberacea.

6. The method of claim 1 wherein said Free-B-Ring flavonoid is isolated from a plant genus selected from the group consisting of *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*.

7. The method of claim 1 wherein said flavan is isolated from a plant species selected from the group consisting of the *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium*.

8. The method of claim 1 wherein said Free-B-Ring flavonoid is isolated from a plant or plants in the *Scutellaria* genus of plants and said flavan is isolated from a plant or plants in the *Acacia* genus of plants.

9. The method of claim 1 wherein the composition is administered in a dosage selected from 0.01 to 200 mg/kg of body weight on a daily basis.

10. The method of claim 1 wherein the routes of the administration are selected from the group consisting of oral, topical, suppository, intravenous, and intradermic, intragaster, intramusclar, intraperitoneal and intravenous administration.

* * * * *